(12) United States Patent
Srivastava

(10) Patent No.: US 6,187,312 B1
(45) Date of Patent: Feb. 13, 2001

(54) COMPOSITIONS AND METHODS USING COMPLEXES OF HEAT SHOCK PROTEIN 90 AND ANTIGENIC MOLECULES FOR THE TREATMENT AND PREVENTION OF INFECTIOUS DISEASES

(75) Inventor: Pramod K. Srivastava, Riverdale, NY (US)

(73) Assignee: Fordham University, Bronx, NY (US)

( * ) Notice: Under 35 U.S.C. 154(b), the term of this patent shall be extended for 0 days.

(21) Appl. No.: 09/150,040

(22) Filed: Sep. 9, 1998

Related U.S. Application Data

(62) Division of application No. 08/527,391, filed on Sep. 13, 1995, now Pat. No. 5,837,251.

(51) Int. Cl.$^7$ ......................... A61K 39/00; A61K 39/002; A61K 39/38; A61K 39/385

(52) U.S. Cl. ..................................... 424/193.1; 424/184.1; 424/194.1; 424/196.11; 424/197.11; 424/265.1; 424/274.1; 424/277.1

(58) Field of Search .............................. 424/184.1, 193.1, 424/196.11, 197.11, 265.1, 274.1, 194.1

(56) References Cited

U.S. PATENT DOCUMENTS

| | | |
|---|---|---|
| 4,690,915 | 9/1987 | Rosenberg . |
| 5,188,964 | 2/1993 | McGuire et al. . |
| 5,232,833 | 8/1993 | Sanders et al. . |
| 5,348,945 | 9/1994 | Berberian et al. . |
| 5,747,332 | 5/1998 | Wallen et al. . |
| 5,750,119 | 5/1998 | Srivastava . |
| 5,830,464 | 11/1998 | Srivastava . |
| 5,837,251 | 11/1998 | Srivastava . |
| 5,935,576 | 8/1999 | Srivastava . |
| 5,948,646 | 9/1999 | Srivastava . |
| 5,961,979 | 10/1999 | Srivastava et al. . |
| 5,985,270 | 11/1999 | Srivastava . |
| 5,997,873 | 12/1999 | Srivastava et al. . |
| 6,007,821 | 12/1999 | Srivastava et al. . |
| 6,017,540 | 1/2000 | Srivastava et al. . |
| 6,017,544 | 1/2000 | Srivastava . |
| 6,030,618 | 2/2000 | Srivastava . |
| 6,048,530 | 4/2000 | Srivastava . |

FOREIGN PATENT DOCUMENTS

| | | |
|---|---|---|
| 196 02 985 A1 | 7/1997 | (DE) . |
| 2 251 186A | 7/1992 | (GB) . |
| WO 89/12455 | 12/1989 | (WO) . |
| WO 90/02564 | 3/1990 | (WO) . |
| WO 91/15572 | 10/1991 | (WO) . |
| WO 92/01717 | 2/1992 | (WO) . |
| WO 92/08484 | 5/1992 | (WO) . |
| WO 92/08488 | 5/1992 | (WO) . |
| WO 93/14118 | 7/1993 | (WO) . |
| WO 93/17712 | 9/1993 | (WO) . |
| WO 93/18146 | 9/1993 | (WO) . |
| WO 93/18147 | 9/1993 | (WO) . |
| WO 93/18150 | 9/1993 | (WO) . |
| WO 93/21529 | 10/1993 | (WO) . |
| WO 93/24136 | 12/1993 | (WO) . |
| WO 94/03208 | 2/1994 | (WO) . |
| WO 94/04676 | 3/1994 | (WO) . |
| WO 94/11513 | 5/1994 | (WO) . |
| WO 94/29459 | 12/1994 | (WO) . |
| WO 97/06685 | 2/1997 | (WO) . |
| WO 97/06821 | 2/1997 | (WO) . |
| WO 97/06828 | 2/1997 | (WO) . |
| WO 97/26910 | 7/1997 | (WO) . |
| WO 98/12208 | 3/1998 | (WO) . |

OTHER PUBLICATIONS

Aldovini et al. (1992) "The New Vaccines", *Technology Review* pp. 24–31.

Barrios et al. (1992) "Mycobacterial heat–shock proteins as carrier molecules. II: The use of the 70–kDa mycobacterial heat–shock protein as carrier for conjugated vaccines that can circumvent the need for adjuvants and *Bacillus Calmette Gueérin* priming", *Eur. J. Immunol.* 22:1365–1372.

Basombrio (1970) "Search for common antigenicities among twenty–five sarcomas induced by methylcholanthrene", *The Institute for Cancer Research* 30:2–2462.

Blachere et al. (1993) "Heat Shock Protein Vaccines Against Cancer," *Journal of Immunotherapy* 14:352–356.

Blachere and Srivastava (1993) "Immunization with GP96 heat shock proteins isolated from tumors or influenza virus infected cells elicits MHC–restricted, antigen–specific cytotoxic T lymphocytes against the corresponding cells", *J. Cellular Biochem. Keystone Symposia* NZ502, p. 124.

Boon, (1992) "Toward a genetic analysis of tumor rejection antigens", *Advances in Cancer Research* 58:177–210.

(List continued on next page.)

*Primary Examiner*—Geetha P. Bansal
(74) *Attorney, Agent, or Firm*—Pennie & Edmonds LLP

(57) ABSTRACT

The invention relates to methods and compositions for eliciting an immune response and the prevention and treatment of primary and metastatic neoplastic diseases and infectious diseases. The methods of the invention comprise administering a composition comprising an effective amount of a complex, in which the complex consists essentially of a heat shock protein (hsp) noncovalently bound to an antigenic molecule. "Antigenic molecule" as used herein refers to the peptides with which the hsps are endogenously associated in vivo as well as exogenous antigens/immunogens (i.e., with which the hsps are not complexed in vivo) or antigenic/immunogenic fragments and derivatives thereof. In a preferred embodiment, the complex is autologous to the individual. The effective amounts of the complex are in the range of 10–600 micrograms for complexes comprising hsp70, 50–1000 micrograms for hsp90, and 10–600 micrograms for gp96. The invention also provides a method for measuring tumor rejection in vivo in an individual, preferably a human, comprising measuring the generation by the individual of MHC Class I-restricted CD8+cytotoxic T lymphocytes specific to the tumor. Methods of purifying hsp70-peptide complexes are also provided.

9 Claims, 8 Drawing Sheets

OTHER PUBLICATIONS

Figure 1A:
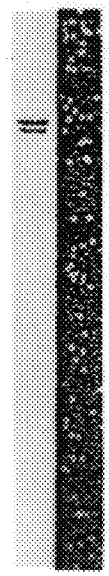

Cohen (1993) "Cancer Vaccines Get A Shot In The Arm", *Science* 262:841–843.

Craig (1993) "Chaperones: Helpers Along the Pathways to Protein Folding", *Science* 260:1902–1904.

Elliott et al. (1990) "Naturally Processed Peptides", *Nature* 348:195–197.

Falk et al. (1991) "Allele–specific Motifs Revealed by Sequencing of Self–peptides Eluted from MHC Molecules", *Nature* 351:290–296.

Falk et al. (1990) "Cellular Peptide Composition Governed by Major Histocompatibility Complex Class I Molecules", *Nature* 348:248–251.

Fedweg and Srivastava, (1993) "Evidence for biochemical heterogeneity of gp96 heat shock protein/tumor rejecion antigen", J. Cellular Biochem. Supp. 17D NZ 206, p. 108.

Flynn et al. (1989) "Peptide binding and release by proteins implicated as catalysts of protein assembly", *Science* 245:385–390.

Flynn et al. (1991) "Peptide–binding Specificity of the Molecular Chaperone BiP", *Nature* 353:726–730.

Franklin (1993) "Making vaccines fit the cancer", *New Scientist* 140:17.

Gething et al. (1992) "Protein Folding in the Cell", *Nature* 355:33–45.

Globerson and Feldman (1964) "Antigenic specificity of benzo[a]pyrene–induced sarcomas", *Journal of the National Cancer Institute* 32(6):1229–1242.

Jakob et al. (1993) "Small Heat Shock Proteins Are Molecular Chaperones", *J. Biol. Chem.* 268:1517–1520.

Jardetzky et al. (1991) "Identification of Self Peptides Bound to Purified HLA–B27", *Nature* 353:326–329.

Lakey et al (1987) "Identification of a peptide binding protein that plays a role in antigen presentation", *Proc. Natl. Acad. Sci. USA* 84:1659–1663.

Lanzavecchia (1993) "Identifying Strategies for Immune Intervention", *Science* 260:937–944.

Lévy (1991) "ATP is Required for In Vitro Assembly of MHC Class I Antigens but Not for Transfer of Peptides across the ER Membrane", *Cell* 67:265–274.

Li and Srivastava (1993) "Tumor rejection antigen gp96/grp94 is an ATPase: Implications for protein folding and antigen presentation", *EMBO J.* 12(8):3143–3151.

Lindquist and Craig (1988) "The heat–shock proteins", *Ann. Rev. Genet.* 22:631–677.

Luescher et al. (1991) "Specific Binding of Antigenic Peptides to Cell–associated MHC Clas I Molecules", *Nature* 351:72–77.

Lukacs et al. (1993) "Tumor cells transfected with a bacterial heat–shock gene lose tumorigenicity and induce protection against tumors", *J. Exp. Med.* 178:343–348.

Lussow et al. (1991) "Mycobacterial heat–shock proteins as carrier molecules", *Eur. J. Immunol.* 21:2297–2302.

Madden et al. (1991) "The Structure of HLA–B27 Reveals Nonamer Self–peptides Bound in an Extended Conformation", *Nature* 353:321–325.

Maki et al. (1993) "Mapping of the Genes for Human Endoplasmic Reticular Heat Shock Protein gp96/grp94", *Somatic Cell Mol. Genetics* 19(1):73–81.

Maki et al. (1990) "Human homologue of murine tumor rejection antigen gp96: 5'–Regulatory and coding regions and relationship to stress–induced proteins", *Proc. Natl. Acad. Sci. USA* 87:5658–5663.

McCall et al. (1989) "Biotherapy: A New Dimension in Cancer Treatment", *Biotechnology* 7:231–240.

Melnick (1985) "Virus Vaccines: An Overview", Proceedings of the First Annual Southwest Foundation for Biomedical Research International Symposium, Houston, Texas, Nov. 8–10, 1984, *American Society for Microbiology* pp. 1–13.

Nelson et al. (1992) "The Translation Machinery and 70 kd Heat Shock Protein Cooperate in Protein Synthesis", *Cell* 71:97–105.

Palladino et al. (1987) "Expression of shared tumor–specific antigen by two chemically induced BALB/c sarcomas", *Cancer Research* 47:5074–5079.

Prehn and Main (1957) "Immunity to methylcholanthrene–induced sarcomas", *Journal of the National Cancer Institute* 18(6):769–778.

Rothman (1989) "Polypeptide Chain Binding Proteins: Catalysts of Protein Folding and Related Processes in Cells", *Cell* 59:591–601.

Rötzschke et al. (1990) "Isolation and Analysis of Naturally Processed Viral Peptides as Recognized by Cytotoxic T cells", *Nature* 348:248–251.

Salk et al. (1993) "A Strategy for Prophylactic Vaccination Against HIV", *Science* 260:1270–1272.

Schumacher et al. (1991) "Peptide Selection by MHC Class I Molecules", *Nature* 350:703–706.

Srivastava et al. (1991) "Protein Tumor Antigens", *Curr. Opin. Immunol.* 3:654–658.

Srivastava et al. (1984) "The Serologically Unique Cell Surface Antigen of Zajdela Ascitic Hepatoma is also its Tumor–Associated Transplantation Antigen", *Int. J. Cancer* 33:417–422.

Srivastava et al. (1989) "Identification of a Human Homologue of the Murine Tumor Rejection Antigen GP96," *Cancer Res.* 49:1341–1343.

Srivastava et al. (1988) "Individually Distinct Transplantation Antigens of Chemically Induced Mouse", *Immunology Today* 9:78–83.

Srivastava et al. (1988) "Chromosonal Assignment of the Gene Encoding the Mouse Tumor Rejection Antigen gp96", *Immunogenetics* 28:205–207.

Srivastava et al. (1987) "5'–Structural analysis of genes encoding polymorphic antigens of chemically induced tumors", *Proc. Natl. Acad. Sci. USA* 84:3807–3811.

Srivastava et al. (1993) "Peptide–Binding Heat Shock Proteins in the Endoplasmic Reticulum: Role in Immune Response to Cancer and in Antigen Presentation", *Advances in Cancer Research* 62:153–177.

Srivastava and Maki (1991) "Stress–induced proteins in immune response cancer", *Microbiol. Immunol.* 167:109–123.

Srivastava and Heike (1991) "Tumor–specific immunogenicity of stress–induced proteins: Convergence of two evolutionary pathways of antigen presentation?", *Seminars in Immunology* 3:57–64.

Srivastava et al. (1986) "Tumor rejection antigens of chemically induced sarcomas of inbred mice", *Proc. Natl. Acad. Sci. USA* 83:3407–3411.

Subbarao et al. (1992) "A General Overview of Viral Vaccine Development," *Genetically Engineered Vaccines* 327:51–57.

Szikora et al. (1990) "Structure of the gene of tum–transplantation antigen P35B presence of a point mutation in the agenic allele", *EMBO J.* 9(4):1041–1050.

Udono (1993) "Heat shock proteins HSP70, HSP90 and GP96 elicit tumor specific immunity to the tumors from which they are isolated", *J. Cell. Biochem.* Suppl. 17D:113 (Abstract NZ225).

Udono et al. (1993) "Heat Shock Protein 70–associated Peptides Elicit Specific Cancer Immunity", *J. Exp. Med.* 178:1391–1396.

Ullrich et al. (1986) "A mouse tumor–specific transplantation antigen is a heat shock–related protein", *Proc. Natl. Acad. Sci. USA* 83:3121–3125.

Vanbuskirk et al. (1989) "peptide binding protein having a role in antigen presentation is a member of the hsp70 heat shock family", *J. Exp. Med.* 170:1799–1809.

Welch et al. (1982), "Purification of the Major Mammalian Heat Shock Proteins", *J. Biol. Chem.* 257:14949–14959.

Welch et al. (1985) "Rapid Purification of Mammalian 70,000–Dalton Stress Proteins: Affinity of the Proteins for Nucleotides", *Mol. Cell. Biol.* 5:1229–1237.

Welch (1993) "How Cells Respond to Stress", *Scientific American* pp. 56–64.

Young (1990) "Stress Proteins and Immunology", *Annu. Rev. Immunol.* 8:401–420.

Yu et al. (1991) "Sequence Analysis of Peptides Bound to MHC Class II Molecules", *Nature* 353:622–627.

Blachere et al., 1993, "Immunization with GP96 heat shock proteins isolated from tumors or influenza virus infected cells elicits MHC–restricted, antigen–specific cytotoxic T lymphocytes against the corresponding cells/antigens", *J. Cell Biochem.* Suppl. 17D:124 (Abstract NZ 502).

Levinson et al., 1979 "Metal Binding Drugs Induce Synthesis of Four Proteins in Normal Cells", *Biol. Trace Element Research* 1:15–23.

Martin et al., 1986, "Role of Murine Tumor Models in Cancer Treatment Research", *Cancer Res.* 46:2189–2192.

Mulé et al., 1984, "Adoptive Immunotherapy of Established Pulmonary Metastases with LAK cells and Recombinant Interleukin–2", *Science* 225: 1487–1489.

Nieland et al., 1996, "Isolation of an immunodominant viral peptide that is endogenously bound to the stress protein GP96/GRP94", *Proc. Natl. Acad. Sci. USA* 93: 6135–6139.

Srivastava et al., 1993, "Evidence for peptide–chaperoning by the endoplasmic reticular heat shock protein GP96: Implications for vaccination against cancer and infectious diseases", *J. Cell Biochem.* Suppl. 17D:94 (Abstract NZ014).

Suto, R. and Srivastava, P.K., 1995, "A Mechanism for the Specific Immunogenicity of Heat Shock Protein–Chaperoned Peptides", *Science* 269: 1585–1588.

Thomas et al., 1982, "Molecular and Cellular Effects of Heat Shock and Related Treatments of Mammalian Tissue–Culture Cells", Cold Springs Harbor Symp Quant. Biol. 46: 985–996.

Arnold et al., 1995, "Cross–priming of minor histocompatibility antigen–specific cytotoxic T cells upon immunization with the heat shock protein gp96", *J. Exp. Med.* 182:885–889.

Cole & Ostrand–Rosenburg, 1991, "Rejection of allogeneic tumor is not determined by host responses to MHC class I molecules and is mediated by $CD4^-CD8^+$ T lymphocytes that are not lytic for the tumor", *Cellular Immunol.* 134:480–490.

Engman et al., 1990, "Human humoral immunity to hsp70 during *Trypanosoma cruzi* infection", *J. of Immunol.* 144:3987–3991.

Estes et al., 1993, "Characterization of an unusual cell type ($CD4^+CD3^-$) expanded by helminth infection and related to the parasite stress response", *J. of Immunol.* 150:1846–1856.

C. Ezzel, 1995, "Cancer 'Vaccines': An idea whose time has come?", *J. NIH Res.* 7:46–49.

Jindal & Young, 1992, "Vaccinia virus infection induces a stress response that leads to association of Hsp70 with viral proteins", *J. of Virol.* 66:5357–5362.

Johnson et al., 1989, "The 86–kilodalton antigen from *Schistosoma mansoni* is a heat–shock protein homologous to yeast HSP–90", *Mol. and Biochem. Parasitol.* 36:19–28.

Luft et al., 1991, "Immunologic and structural characterization of the dominant 66– to 73–kDa antigens of *Borrelia burgdoferi*", *J. of Immunol.* 146:2776–2782.

Srivastava et al., 1994, "Heat shock proteins transfer peptides during antigen processing and CTL priming", *Immunogenetics* 39:93–98.

Udono & Srivastava, 1994, "Comparison of tumor–specific immunogenicities of stress–induced proteins gp96, hsp90, and hsp70", *J. of Immunol.* 152:5398–5403.

Udono et al., 1994, "Cellular requirements for tumor–specific immunity elicited by heat shock proteins: Tumor rejection antigen gp96 primes $CD8^+$ T cells in vivo", *PNAS USA* 91:3077–3081.

White et al., 1988, "Differential distribution of the adenovirus E1A proteins and colocalization of E1A with the 70–kilodalton cellular heat shock protein in infected cells", *J. of Virol.* 62:4153–4166.

International Search Report, Related PCT Application No. PCT/US96/14557.

Written Opinion dated Jul. 1, 1997, Related PCT Application No. PCT/US96/14557.

Sadis and Hightower, 1992, "Unfolded proteins stimulate molecular chaperone Hsc70 ATPase by accelerating ADP/ATP exchange", *Biochemistry* 31:9406–9412.

COMPOSITIONS AND METHODS USING COMPLEXES OF HEAT SHOCK PROTEIN 90 AND ANTIGENIC MOLECULES FOR THE TREATMENT AND PREVENTION OF INFECTIOUS DISEASES

This is a division of application Ser. No. 08/527,391, filed Sep. 13, 1995 now U.S. Pat. 5,837,251.

This invention was made with government support under grant numbers CA44786 and CA64394 awarded by the National Institutes of Health. The government has certain rights in the invention.

TABLE OF CONTENTS
1. INTRODUCTION
2. BACKGROUND OF THE INVENTION
   2.1. Tumor-Specific Immunogenicities of Heat Shock/Stress Proteins hsp70. hsp90 and gp96
   2.2. Pathobiology of Cancer
   2.3. Immunotherapy
      2.3.1. Interleukins (IL-2, IL-4 and IL-6)
      2.3.2. Tumor Necrosis Factor
      2.3.3. Interferons
   2.4. Pharmacokinetic Models for Anticancer Chemotherapeutic and Immunotherapeutic Drugs: Extrapolation and Scaling of Animal Data to Humans
3. SUMMARY OF THE INVENTION
4. BRIEF DESCRIPTION OF FIGURES
5. DETAILED DESCRIPTION OF THE INVENTION
   5.1. Dosage Regimens
   5.2. Therapeutic Compositions for Immune Responses to Cancer
      5.2.1. Preparation and Purification of Hsp 70-Peptide Complexes
      5.2.2. Preparation and Purification of Hsp 90-peptide complexes
      5.2.3. Preparation and Purification of gp96-Peptide Complexes
      5.2.4. Isolation of Antigenic/Immunogenic Components
         5.2.4.1 Peptides From Stress Protein-Peptide Complexes
         5.2.4.2 Peptides from MHC-Peptide Complexes
      5.2.5 Exogenous Antigenic Molecules
      5.2.6 In Vitro Production of Stress Protein-Antigenic Molecule Complexes
      5.2.7 Determination of Immunogenicity of Stress Protein-Peptide Complexes
   5.3. Formulation
   5.4 Target Infectious Diseases
   5.5. Target Cancers
      5.5.1. Colorectal Cancer Metastatic to the Liver
      5.5.2. Hepatocellular Carcinoma
      5.5.3. Breast Cancer
   5.6. Autologous Embodiment
   5.7. Prevention and Treatment of Primary and Metastatic Neoplastic Diseases
   5.8. Monitoring of Effects During Cancer Prevention and Immunotherapy
      5.8.1. Delayed Hypersensitivity Skin Test
      5.8.2. Activity of Cytolytic T-lymphocytes In Vitro
      5.8.3. Levels of Tumor Specific Antigens
      5.8.4. Computed Tomographic (CT) Scan
      5.8.5. Measurement of Putative Biomarkers
      5.8.6. Sonogram
6. EXAMPLE Administration of Hsp-Peptide Complexes in two UV-Induced Carcinoma Models in Mice
   6.1 Prevention Modality
   6.2 Treatment Modality
   6.3 Measuring Generation of MHC Class I Restricted $CD8^+$ CTLs Provides an Assay for In Vivo Tumor Rejection
   6.4 GP96-Peptide Complexes Elicit a Memory T Cell Response

7. EXAMPLE

Administration of Hsp-Peptide Complexes in the Treatment of Hepatocellular Carcinoma

8. EXAMPLE

Administration of Hsp-Peptide Complexes in the Treatment of Colorectal Cancer

9. EXAMPLE

Method for Rapid Purification of Peptide-Associated Hsp70
   9.1 Method and Results

1. INTRODUCTION

The present invention relates to methods and compositions for the prevention and treatment of infectious diseases, primary and metastatic neoplastic diseases, including, but not limited to human sarcomas and carcinomas. In the practice of the prevention and treatment of infectious diseases and cancer, compositions of complexes of heat is shock/stress proteins (hsps) including, but not limited to, hsp70, hsp90, gp96 alone or in combination with each other, noncovalently bound to antigenic molecules, are used to augment the immune response to genotoxic and nongenotoxic factors, tumors and infectious agents.

2. BACKGROUND OF THE INVENTION

The era of tumor immunology began with experiments by Prehn and Main, who showed that antigens on the methylcholanthrene (MCA)-induced sarcomas were tumor specific in that transplantation assays could not detect these antigens in normal tissue of the mice (Prehn, R. T., et al., 1957, *J. Natl. Cancer Inst.* 1:769–778). This notion was confirmed by further experiments demonstrating that tumor specific resistance against MCA-induced tumors can be elicited in the autochthonous host, that is, the mouse in which the tumor originated (Klein, G., et al., 1960, *Cancer Res.* 20:1561–1572).

In subsequent studies, tumor specific antigens were also found on tumors induced with other chemical or physical carcinogens or on spontaneous tumors (Kripke, M. L., 1974, *J. Natl. Cancer Inst.* 53:1333–1336; Vaage, J., 1968, *Cancer Res.* 28:2477–2483; Carswell, E. A., et al., 1970, *J. Natl. Cancer Inst.* 44:1281–1288). Since these studies used protective immunity against the growth of transplanted tumors as the criterion for tumor specific antigens, these antigens are also commonly referred to as "tumor specific transplantation antigens" or "tumor specific rejection antigens." Several factors can greatly influence the immunogenicity of the tumor induced, including, for example, the specific type of carcinogen involved, immunocompetence of the host and latency period (Old, L. J., et al., 1962, *Ann. N.Y. Acad. Sci.* 101:80–106; Bartlett, G. L., 1972, *J. Natl. Cancer Inst.* 49:493–504).

Most, if not all, carcinogens are mutagens which may cause mutation, leading to the expression of tumor specific antigens (Ames, B. N., 1979, *Science* 20:587–593; Weisburger, J. H., et al., 1981, *Science* 21:401–407). Some carcinogens are immunosuppressive (Malmgren, R. A., et al., 1952, *Proc. Soc. Exp. Biol. Med.* 79:484–488). Experimental evidence suggests that there is a constant inverse correlation between immunogenicity of a tumor and latency period (time between exposure to carcinogen and tumor appearance) (Old, L. J., et al., 1962, *Ann. N.Y. Acad. Sci.* 101:80–106; and Bartlett, G. L., 1972, *J. Natl. Cancer Inst.* 49:493–504). Other studies have revealed the existence of tumor specific antigens that do not lead to rejection, but, nevertheless, can potentially stimulate specific immune responses (Roitt, I., Brostoff, J and Male, D., 1993, Immunology, 3rd ed., Mosby, St. Louis, pps. 17.1–17.12).

2.1. Tumor-Specific Immunogenicities of Heat Shock/Stress Proteins hsp70. hsp90 and gp96

Srivastava et al. demonstrated immune response to methylcholanthrene-induced sarcomas of inbred mice (1988, *Immunol. Today* 9:78–83). In these studies it was found that the molecules responsible for the individually distinct immunogenicity of these tumors were identified as cell-surface glycoproteins of 96 kDa (gp96) and intracellular proteins of 84 to 86 kDa (Srivastava, P. K., et al., 1986, *Proc. Natl. Acad. Sci. USA* 83:3407–3411; Ullrich, S. J., et al., 1986, *Proc. Natl. Acad. Sci. USA* 83:3121–3125. Immunization of mice with gp96 or p84/86 isolated from a particular tumor rendered the mice immune to that particular tumor, but not to antigenically distinct tumors. Isolation and characterization of genes encoding gp96 and p84/86 revealed significant homology between them, and showed that gp96 and p84/86 were, respectively, the endoplasmic reticular and cytosolic counterparts of the same heat shock proteins (Srivastava, P. K., et al., 1988, *Immunogenetics* 28:205–207; Srivastava, P. K., et al., 1991, *Curr. Top. Microbiol. Immunol.* 167:109–123). Further, hsp70 was shown to elicit immunity to the tumor from which it was isolated but not to antigenically distinct tumors. However, hsp7o depleted of peptides was found to lose its immunogenic activity (Udono, M., and Srivastava, P. K., 1993, *J. Exp. Med.* 1:1391–1396). These observations suggested that the heat shock proteins are not immunogenic per se, but are carriers of antigenic peptides that elicit specific immunity to cancers (Srivastava, P. K., 1993, *Adv. Cancer Res.* 62:153–177).

2.2. Pathobiology of Cancer

Cancer is characterized primarily by an increase in the number of abnormal cells derived from a given normal tissue, invasion of adjacent tissues by these abnormal cells, and lymphatic or blood-borne spread of malignant cells to regional lymph nodes and to distant sites (metastasis). Clinical data and molecular biologic studies indicate that cancer is a multistep process that begins with minor pre-neoplastic changes, which may under certain conditions progress to neoplasia.

Pre-malignant abnormal cell growth is exemplified by hyperplasia, metaplasia, or most particularly, dysplasia (for review of such abnormal growth conditions, see Robbins and Angell, 1976, *Basic Pathology*, 2d Ed., W. B. Saunders Co., Philadelphia, pp. 68–79.) Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

The neoplastic lesion may evolve clonally and develop an increasing capacity for invasion, growth, metastasis, and heterogeneity, especially under conditions in which the neoplastic cells escape the host's immune surveillance (Roitt, I., Brostoff, J and Male, D., 1993, Immunology, 3rd ed., Mosby, St. Louis, pps. 17.1–17.12).

2.3. Immunotherapy

Four-basic cell types whose function has been associated with antitumor cell immunity and the elimination of tumor cells from the body are: i) B-lymphocytes which secrete immunoglobulins into the blood plasma for identifying and labeling the nonself invader cells; ii) monocytes which secrete the complement proteins which are responsible for lysing and processing the immunoglobulin-coated target invader cells; iii) natural killer lymphocytes having two mechanisms for the destruction of tumor cells-antibody-dependent cellular cytotoxicity and natural killing; and iv) T-lymphocytes possessing antigen-specific receptors and each T-lymphocyte clone having the capacity to recognize a tumor cell carrying complementary marker molecules (Schreiber, H., 1989, in *Fundamental Immunology* (ed). W. E. Paul, pp. 923–955).

Several factors can influence the immunogenicity of tumors induced. These factors include dose of carcinogen, immunocompetence of the host, and latency period. Immunocompetence of the host during the period of cancer induction and development can allow the host to respond to immunogenic tumor cells. This may prevent the outgrowth of these cells or select far less immunogenic escape variants that have lost their respective rejection antigen. Conversely, immunosuppression or immune deficiency of the host during carcinogenesis or tumorigenesis may allow growth of highly immunogenic tumors (Schreiber, H., 1989, in *Fundamental Immunology* (ed). W. E. Paul, pp. 923–955).

Three major types of cancer immunotherapy are currently being explored: i) adoptive cellular immunotherapy, ii) in vivo manipulation of patient plasma to remove blocking factors or add tumoricidal factors, and iii) in vivo administration of biological response modifiers (e.g., interferons (IFN; IFN-alpha and IFN-gamma), interleukins (IL; IL-2, IL-4 and IL-6), colony-stimulating factors, tumor necrosis factor (TNF), monoclonal antibodies and other immunopotentiating agents, such as corynebacterium parvum (C. parvum) (Kopp, W. C., et al., 1994, *Cancer Chemotherapy and Biol. Response Modifiers* 15:226–286). There is little doubt that immunotherapy of cancer as it stands is falling short of the hopes invested in it. Although numerous immunotherapeutic approaches have been tested, few of these procedures have proved to be effective as the sole or even as an adjunct form of cancer prevention and treatment.

2.3.1. Interleukins (IL-2, IL-4 and IL-6)

IL-2 has significant antitumor activity in a small percentage of patients with renal cell carcinoma and melanoma. Investigators continue to search for IL-2 based regimens that will increase the response rates in IL-2 responsive tumors, but, for the most part, have neither defined new indications nor settled fundamental issues, such as whether dose intensity is important in IL-2 therapy (Kopp, W. C., et al., 1994, *Cancer Chemotherapy and Biol. Response Modifiers* 15:226–286). Numerous reports have documented IL-2 associated toxicity involving increased nitrate levels and the syndrome of vascular leak and hypotension, analogous to septic shock. In addition, an increased incidence of nonopportunistic bacterial infections and autoimmune complications are frequently accompanied by the antitumor response of IL-2 (Kopp, W. C., et al., 1994, *Cancer Chemotherapy and Biol. Response Modifiers* 15:226–286).

IL-4 and IL-6 are also being tested as antitumor agents either directly or through immunomodulating mechanisms. Dose-limiting toxicities have been observed with both agents in Phase I clinical trials (Gilleece, M. H., et al., 1992, *Br. J. Cancer* 6:204–210, Weber, J., et al., 1993, *J. Clin. Oncol.* 11:499–506).

2.3.2. Tumor Necrosis Factor

The toxicity of systemically administered TNF seriously limits its use for the treatment of cancer. TNF has been most effective when used for regional therapy, in which measures, such as limb isolation for perfusion, are taken to limit the systemic dose and hence the toxicity of TNF. Dose-limiting toxicity of TNF consist of thrombocytopenia, headache, confusion and hypotension (Mittleman, A., et al., 1992, *Inv. New Drugs* 10:183–190).

2.3.3. Interferons

The activity of IFN-α has been described as being modest in a number of malignancies, including renal cell carcinoma, melanoma, hairy cell leukemia low-grade non-Hodgkin's lymphoma, and others. Higher doses of IFN-α are usually associated with higher response rates in some malignancies, but also cause more toxicity. In addition, more and more reports indicate that relapses after successful interferon therapy coincide with formation of neutralizing antibodies against interferon (Ouesada, J. R., et al., 1987, *J. Interferon Res.* 67:678.

2.4. Pharmacokinetic Models for Anticancer Chemotherapeutic and Immunotherapeutic Drugs: Extrapolation and Scaling of Animal Data to Humans The ethical and fiscal constraints which require the use of animal models for most toxicology research also impose the acceptance of certain fundamental assumptions in order to estimate dose potency in humans from dose-response data in animals. Interspecies dose-response equivalence is most frequently estimated as the product of a reference species dose and a single scaling ratio based on a physiological parameter such as body weight, body surface area, maximum life span potential, etc. Most frequently, exposure is expressed as milligrams of dose administered in proportion to body mass in kilograms (mg kg$^{-1}$). Body mass is a surrogate for body volume, and therefore, the ratio milligrams per kilogram is actually concentrations in milligrams per liter (Hirshaut, Y., et al., 1969, *Cancer Res.* 29:1732–1740). The key assumptions which accompany this practice and contribute to its failure to accurately estimate equipotent exposure among various species are: i) that the biological systems involved are homogeneous, "well-stirred volumes" with specific gravity equal to 1.0; ii) that the administered compounds are instantly and homogeneously distributed throughout the total body mass; and iii) that the response of the biological systems is directly proportional only to the initial concentration of the test material in the system. As actual pharmacokinetic conditions depart from these assumptions, the-utility of initial concentration scaling between species declines.

Through pharmacokinetics, one can study the time course of a drug and its metabolite levels in different fluids, tissues, and excreta of the body, and the mathematical relationships required to develop models to interpret such data. It, therefore, provides the basic information regarding drug distribution, availability, and the resulting toxicity in the tissues and hence, specifies the limitation in the drug dosage for different treatment schedules and different routes of drug administration. The ultimate goal of the pharmacokinetic studies of anticancer drugs is thus to offer a framework for the design of optimal therapeutic dosage regimens and treatment schedules for individual patients.

The currently utilized guidelines for prescription have evolved gradually without always having a complete and explicit justification. In 1966, Freireich and co-workers proposed the use of surface area proportions for interspecies extrapolation of the acute toxicity of anticancer drugs. This procedure has become the method of choice for many risk assessment applications (Freireich, E. J., et al., 1966, *Cancer Chemotherapy Rep.* 50:219–244). For example, surface area scaling is the basis of the National Cancer Institute's interspecies extrapolation procedure for anti-cancer drugs (Schein, P. S., et al., 1970, *Clin. Pharmacol. Therap.* 11:3–40; Goldsmith, M. A., et al., 1975, *Cancer Res.* 35:1354–1364). In accepting surface area extrapolation, the tenuous basis for initial concentration scaling has been replaced by an empirical approach. The basic formula used for estimating prescription of cancer chemotherapy per body surface area (BSA) is BSA=k×kg$^{2/3}$, in which k is a constant that differs for each age group and species. For example, the k value for adult humans is 11, while for mice it is 9 (see Quiring, P., 1955, *Surface area determination,* in Glasser E. (ed.) Medical Physics I Chicago: Medical Year Book, p. 1490 and Vriesendorp, H. M., 1985, *Hematol.* (Supplm. 16) 11:57–63). The major attraction of expressing cancer chemotherapy per m$^2$ BSA appears to be that it offers an easily remembered simplification, i.e., equal doses of drug per m$^2$ BSA will produce approximately the same effect in comparing different species and age groups. However, simplicity is not proof and alternative methods for estimating prescription of anticancer drugs appear to have a better scientific foundation, with the added potential for a more effective use of anticancer agents (Hill, J. A., et al., 1989, *Health Physics* 57:395–401).

The effectiveness of an optimal dose of a drug used in chemotherapy and/or immunotherapy can be altered by various factors, including tumor growth kinetics, drug resistance of tumor cells, total-body tumor cell burden, toxic effects of chemotherapy and/or immunotherapy on cells and tissues other than the tumor, and distribution of chemotherapeutic agents and/or immunotherapeutic agents within the tissues of the patient. The greater the size of the primary tumor, the greater the probability that a large number of cells (drug resistant and drug sensitive) have metastasized before diagnosis and that the patient will relapse.

Some metastases arise in certain sites in the body where resistance to chemotherapy is based on the limited tissue distribution of chemotherapeutic drugs administered in standard doses. Such sites act as sanctuaries that shield the cancer cells from drugs that are circulating in the blood; for example, there are barriers in the brain and testes that impede drug diffusion from the capillaries into the tissue. Thus, these sites may require special forms of treatment such as immunotherapy, especially since immunosuppression is characteristic of several types of neoplastic diseases.

3. SUMMARY OF THE INVENTION

The methods of the invention comprise methods of eliciting an immune response in an individual in whom the treatment or prevention of cancer is desired by administering a composition comprising an effective amount of a complex in which the complex consists essentially of a heat shock protein (hsp) noncovalently bound to an antigenic molecule. The amounts of the complex are within ranges of effective dosages, discovered by the present inventor to be effective, and which are surprisingly smaller than those amounts predicted to be effective by extrapolation by prior art methods from dosages used in animal studies. In a preferred embodiment, the complex is autologous to the individual; that is, the complex is isolated from the cancer cells of the individual himself (e.g., preferably prepared from tumor biopsies of the patient). Alternatively, the hsp and or the antigenic molecule can be isolated from the individual or from others or by recombinant production methods using a cloned hsp originally derived from the individual or from others. "Antigenic molecule" as used herein refers to the peptides with which the hops are endogenously associated in vivo (e.g., in precancerous or cancerous tissue), as well as exogenous antigens/immunogens (i.e., with which the hsps are not complexed in vivo) or antigenic/immunogenic fragments and derivatives thereof. Such exogenous antigens and fragments and derivatives (both peptide and non-peptide) thereof for use in complexing with hsps, can be selected from among those known in the art, as well as those readily identified by standard immunoassays known in the art by detecting the ability to bind antibody or MHC molecules (antigenicity) or generate immune response (immunogenicity).

The invention also provides a method for measuring tumor rejection in vivo in an individual, preferably a human, comprising measuring the generation by the individual of MHC Class I-restricted $CD8^+$ cytotoxic T lymphocytes specific to the tumor.

The invention provides methods for determining doses for treating infectious diseases or for human cancer immunotherapy by evaluating the optimal dose of complexes of hsps noncovalently bound to antigenic molecules in experimental tumor models and extrapolating the data. The present invention relates to methods and compositions for prevention and treatment of primary and metastatic neoplastic diseases.

Specific therapeutic regimens, pharmaceutical compositions, and kits are provided by the invention. In contrast to the prior art, the therapeutic regimen, and corresponding pharmaceutical compounds of the present invention are not based on body weight or surface area of the patient. The present inventor has discovered that a dosage substantially equivalent to that seen to be effective in smaller non-human mammals (e.g., mice) is effective for human administration, optionally subject to a correction factor not exceeding a fifty fold increase, based on the relative lymph node sizes in such mammals and in humans. Pharmaceutical formulations are provided, based on a newly-discovered extrapolation and scaling of animal dosage to human, comprising compositions of complexes of antigenic molecules and heat shock/stress proteins, including but not limited to hsp70, hsp90, gp96 either alone or in combination. specifically, interspecies dose-response equivalence for hsp noncovalently bound to antigenic molecules for a human dose is estimated as the product of the therapeutic dosage observed in mice and a single scaling ratio, not exceeding a fifty fold increase.

The present invention encompasses methods for prevention and treatment of cancer by enhancing the host's immune competence and activity of immune effector cells. Furthermore, the invention provides methods for evaluating the efficacy of drugs in enhancing immune responses for treatment and monitoring the progress of patients participating in clinical trials for the treatment of primary and metastatic neoplastic diseases.

Immunotherapy using the therapeutic regimens of the invention, by administering such complexes of heat shock/ stress proteins noncovalently bound to antigenic molecules, can induce specific immunity to tumor cells, and leads to regression of the tumor mass. Cancers which are responsive to specific immunotherapy by the heat shock/stress proteins of the invention include but are not limited to human sarcomas and carcinomas. In a specific embodiment, hsp-antigenic molecule complexes are allogeneic to the patient; in a preferred embodiment, the hsp-antigenic are autologous to (derived from) the patient to whom they are administered.

Particular compositions of the invention and their properties are described in the sections and subsections which follow. A preferred composition comprises hsp-peptide complexes isolated from the tumor biopsy of the patient to whom the composition is to be administered. Such a composition which comprises hsp70, hsp90 and/or gp96 demonstrates strong inhibition of a variety of tumors in mammals. Moreover, the therapeutic doses that are effective in the corresponding experimental model in rodents as described infra, in Section 6 can be used to inhibit the in vivo growth of colon and liver cancers in human cancer patients as described in Section 7, infra. Preferred is compositions comprising hsp70, hsp90 and/or gp96 which preferably exhibit no toxicity when administered to human subjects are also described.

In another embodiment, the methods further optionally comprise administering biological response modifiers, e.g., IFN-α, IFN-γ, IL-2, IL-4, IL-6, TNF, or other cytokine growth factors affecting the immune cells, in combination with the hsp complexes.

In addition to cancer therapy, the complexes of hsps noncovalently bound to antigenic molecules can be utilized for the prevention of a variety of cancers, e.g., in individuals who are predisposed as a result of familial history or in individuals with an enhanced risk of cancer due to environmental factors.

An improved method for purification of hsp70-peptide complexes from cells is also provided.

The Examples presented in Sections 6 and 7 below, detail the use according to the methods of the invention of hsp-peptide complexes in cancer immunotherapy in experimental tumor models and in human patients suffering from advanced colon and liver cancer.

4. BRIEF DESCRIPTION OF FIGURES

Figure 1B:
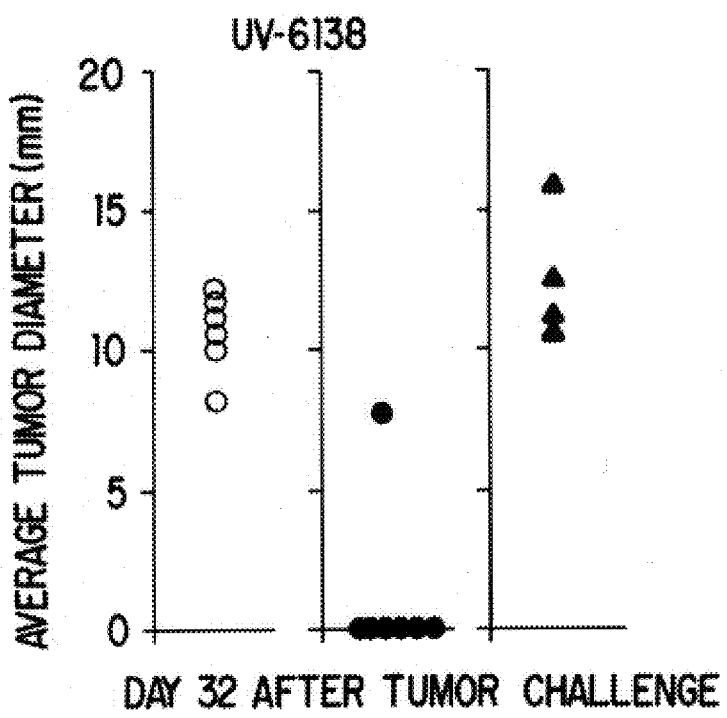
Figure 1C:
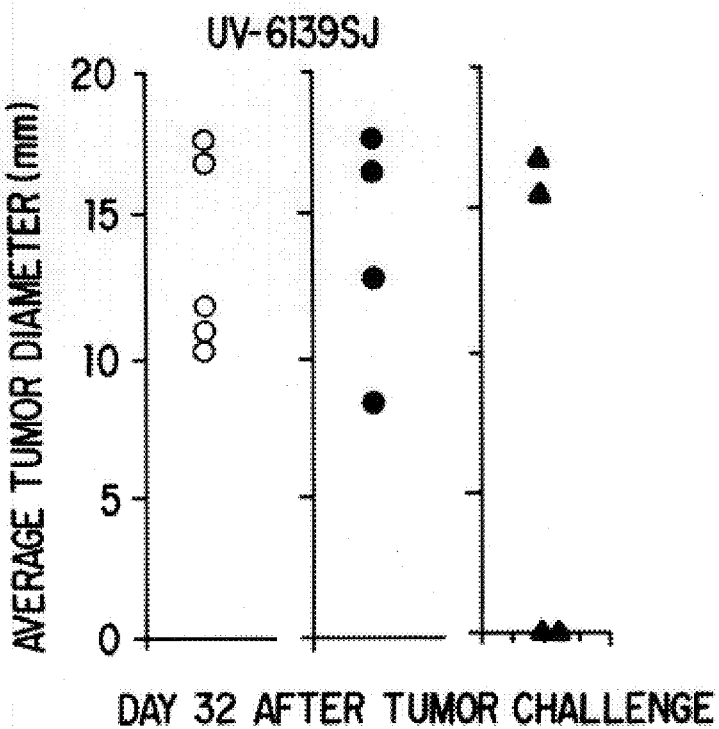

FIG. 1. Effect of Administration of gp96 derived from UV6138 or UV6139SJ carcinomas on tumor growth measured as average tumor diameter (mm).

Panel A: Lane 1, SDS-PAGE profile of gp96 preparation; Lane 2, Immunoblot of lane 1 with antibody specific for gp96.

Panel B (top): All mice were challenged with UV6138 cells. The first group of mice (open circles) received PBS; the second group of mice (solid circles) received gp96 derived from UV6138 cells; and the third group of mice received gp96 derived from UV6139SJ cells.

Panel B (bottom): All mice were challenged with UV6139SJ cells. The first group of mice (open circles) received PBS; the second group of mice (solid circles) received gp96 derived from UV6138 cells; and the third group of mice received gp96 derived from UV6139SJ cells.

Figure 2A:
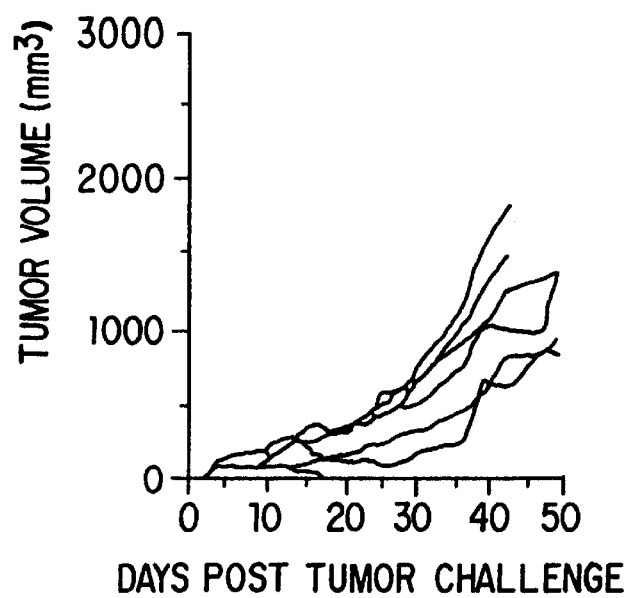
Figure 2B:
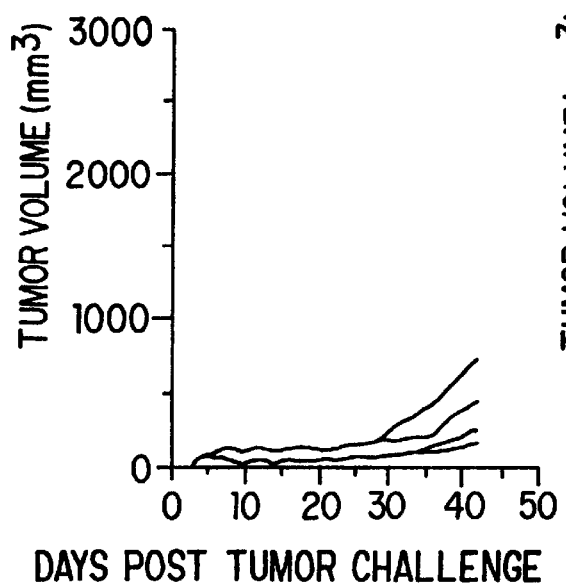
Figure 2C:
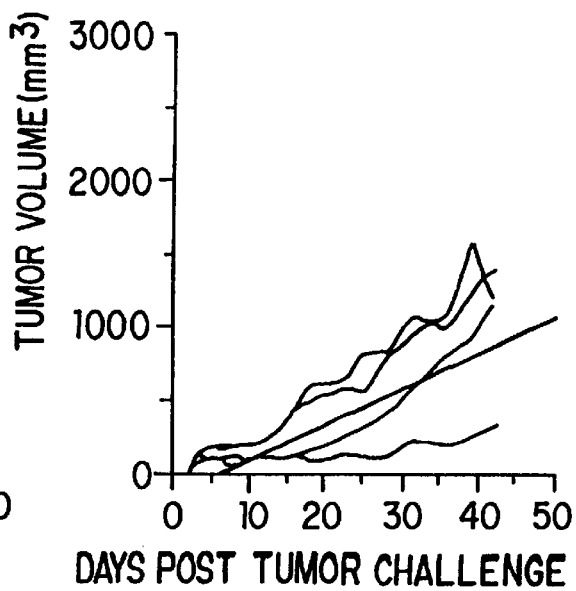

FIG. 2. Effect in tumor-bearing mice of therapeutic administration of gp96 derived from UV6139SJ cells on tumor growth measured as tumor volume (mm$^3$). All mice were challenged with UV6139SJ cells. The first group of mice received no treatment, the second group received gp96 derived form UV6139SJ cells, and the third group received gp96 derived from the liver.

FIG. 3. Vaccination with cognate gp96 preparations elicits MHC class I—restricted CTLs. Mice were immunized with gp96 derived from UV6138 (triangles) or UV6139SJ (rectangles) or with intact tumor cells (circles). Ten days after second immunization, spleens were removed and spleen cells were cocultered in a mixed lymphocyte tumor culture (MLTC) with irradiated tumor cells used for immunization or gp96 preparation. MLTCs were tested for cytotoxicity in a chromium release assay. Open symbols refer to the cytotoxicity in presence of anti-MHC class I specific antibody K44. (A) In vitro cytotoxicity of non-immunized mice (triangle) or mice immunized with 20 microgram of gp96 derived from UV6138 (circle) or UV6139SJ (rectangle) against targets as indicated. (B) In vitro cytotoxicity of non-immunized mice (triangle) or mice immunized twice with 10$^7$ irradiated UV6138 cells (circles) or UV6139SJ cells (rectangles).against targets as indicated.

FIG. 4. Vaccination with cognate gp96 preparations elicits radiation-resistant T cell response. Mice were immunized with gp96 derived from UV6138 (triangles) or UV6139SJ (rectangles) and MLTCs set up as described in legend to FIG. 2, except that mice had been irradiated at 400 rad twelve days after the last vaccination and MLTCs were set up three days after irradiation. Open symbols refer to the cytotoxicity in presence of anti-MHC class I specific antibody K44.

Figure 5B:
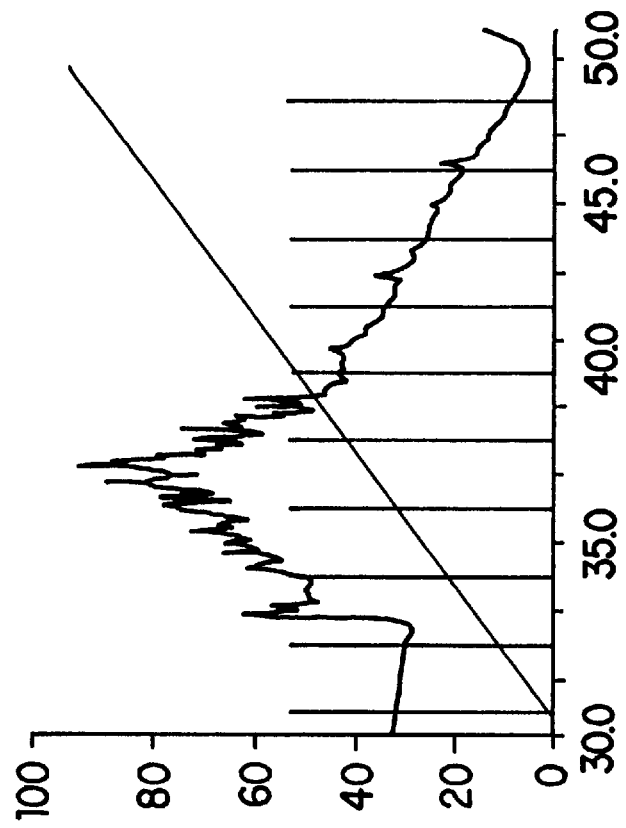
Figure 5A:
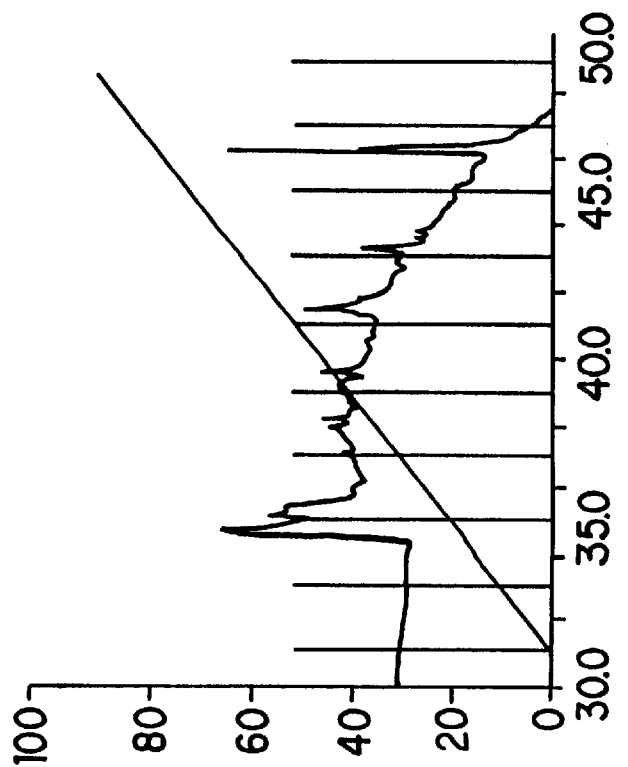

FIGS. 5A–B. FIG. 5A: ATP-bound and ATP eluted hsp70 preparation was found not to be associated with peptides. FIG. 5B: ADP-bound and ADP eluted hsp70 preparation was found to be associated with peptides.

5. DETAILED DESCRIPTION OF THE INVENTION

Methods and compositions for the prevention and treatment of primary and metastatic neoplastic diseases and infectious diseases and for eliciting an immune response in a human individual, are described. The invention is based, in part, on a newly discovered dosage regimen for administration of compositions comprising complexes of hsps noncovalently bound to antigenic molecules.

"Antigenic molecule" as used herein refers to the peptides with which the hops are endogenously associated in vivo (e.g., in infected cells or precancerous or cancerous tissue) as well as exogenous antigens/immunogens (i.e., with which the hsps are not complexed in vivo) or antigenic/immunogenic fragments and derivatives thereof.

The methods of the invention comprise methods of eliciting an immune response in an individual in whom the treatment or prevention of infectious diseases or cancer is desired by administering a composition comprising an effective amount of a complex, in which the complex consists essentially of a hsp noncovalently bound to an antigenic molecule. In a preferred embodiment, the complex is autologous to the individual; that is, the complex is isolated from either from the infected cells or the cancer cells for precancerous cells of the individual himself (e.g., preferably prepared from infected tissues or tumor biopsies of the patient). Alternatively, the complex is produced in vitro (e.g., wherein a complex with an exogenous antigenic molecule is desired). Alternatively, the hsp and/or the antigenic molecule can be isolated from the individual or from others or by recombinant production methods using a cloned hsp originally derived from the individual or from others. Exogenous antigens and fragments and derivatives (both peptide and non-peptide) thereof for use in complexing with hsps, can be selected from among those known in the art, as well as those readily identified by standard immunoassays know in the art by the ability to bind antibody or MHC molecules (antigenicity) or generate immune response (immunogenicity). Complexes of hsps and antigenic molecules can be isolated from cancer or precancerous tissue of a patient, or from a cancer cell line, or can be produced in vitro (as is necessary in the embodiment in which an exogenous antigen is used as the antigenic molecule).

The invention also provides a method for measuring tumor rejection in vivo in an individual, preferably a human comprising measuring the generation by the individual of MHC Class I-restricted CD8$^+$ cytotoxic T lymphocytes specific to the tumor.

The hsps of the present invention that can be used include but are not limited to, hsp70, hsp90, gp96 alone or in combination. Preferably, the hsps are human hsps.

Heat shock proteins, which are also referred to interchangeably herein as stress proteins, useful in the practice of the instant invention can be selected from among any cellular protein that satisfies any one of the following criteria. It is a protein whose intracellular concentration increases when a cell is exposed to a stressful stimuli, it is capable of binding other proteins or peptides, it is capable of releasing the bound proteins or peptides in the presence of adenosine triphosphate (ATP) or low pH, or it is a protein showing at least 35% homology with any cellular protein having any of the above properties.

The first stress proteins to be identified were the heat shock proteins (hsps). As their name implies, hsps are synthesized by a cell in response to heat shock. To date, three major families of hsp have been identified based on molecular weight. The families have been called hsp60, hsp70 and hsp90 where the numbers reflect the approximate molecular weight of the stress proteins in kilodaltons. Many members of these families were found subsequently to be induced in response to other stressful stimuli including, but not limited to, nutrient deprivation, metabolic disruption, oxygen radicals, and infection with intracellular pathogens. (See Welch, May 1993, Scientific American 56–64; Young, 1990, Annu. Rev. Immunol. 8:401–420; Craig, 1993, Science 260:1902–1903; Gething, et al., 1992, Nature 355:33–45; and Lindquist, et al., 1988, Annu. Rev. Genetics 22:631–677), the disclosures of which are incorporated herein by reference. It is contemplated that hsps/stress proteins belonging to all of these three families can be used in the practice of the instant invention.

The major hsps can accumulate to very high levels in stressed cells, but they occur at low to moderate levels in cells that have not been stressed. For example, the highly inducible mammalian hsp70 is hardly detectable at normal temperatures but becomes one of the most actively synthesized proteins in the cell upon heat shock (Welch, et al., 1985, *J. Cell. Biol.* 101:1198–1211). In contrast, hsp90 and hsp60 proteins are abundant at normal temperatures in most; but not all, mammalian cells and are further induced by heat (Lai, et al., 1984, *Mol. Cell. Biol.* 4:2802–10; van Bergen en Henegouwen, et al., 1987, *Genes Dev.* 1:525–31).

Heat shock proteins are among the most highly conserved proteins in existence. For example, DnaK, the hsp70 from *E. coli* has about 50% amino acid sequence identity with hsp70 proteins from excoriates (Bardwell, et al., 1984, *Proc. Natl. Acad. Sci.* 81:848–852). The hsp60 and hsp90 families also show similarly high levels of intra families conservation (Hickey, et al., 1989, *Mol. Cell. Biol.* 9:2615–2626; Jindal, 1989, *Mol. Cell. Biol.* 9:2279–2283). In addition, it has been discovered that the hsp60, hsp70 and hsp90 families are composed of proteins that are related to the stress proteins in sequence, for example, having greater than 35% amino acid identity, but whose expression levels are not altered by stress. Therefore it is contemplated that the definition of stress protein, as used herein, embraces other proteins, muteins, analogs, and variants thereof having at least 35% to 55%, preferably 55% to 75%, and most preferably 75% to 85% amino acid identity with members of the three families whose expression levels in a cell are enhanced in response to a stressful stimulus. The purification of stress proteins belonging to these three families is described below.

The immunogenic hsp-peptide complexes of the invention may include any complex containing an hsp and a peptide that is capable of inducing an immune response in a mammal. The peptides are preferably non covalently associated with the hsp. Preferred complexes may include, but are not limited to, hsp60-peptide, hsp70-peptide and hsp90-peptide complexes. For example, an hsp called gp96 which is present in the endoplasmic reticulum of eukaryotic cells and is related to the cytoplasmic hsp90's can be used to generate an effective vaccine containing a gp96-peptide complex.

Although the hsps can be allogeneic to the patient, in a preferred embodiment, the hsps are autologous to (derived from) the patient to whom they are administered. The hsps and/or antigenic molecules can be purified from natural sources, chemically synthesized, or recombinantly produced. The invention provides methods for determining doses for human cancer immunotherapy by evaluating the optimal dose of hsp noncovalently bound to peptide complexes in experimental tumor models and extrapolating the data. Specifically, a scaling factor not exceeding a fifty fold increase over the effective dose estimated in animals, is used as the optimal prescription method for cancer immunotherapy or vaccination in human subjects.

The invention provides combinations of compositions which enhance the immunocompetence of the host individual and elicit specific immunity against infectious agents or specific immunity against preoplastic and neoplastic cells. The therapeutic regimens and pharmaceutical compositions of the invention are described below. These compositions have the capacity to prevent the onset and progression of infectious diseases and prevent the development of tumor cells and to inhibit the growth and progression of tumor cells indicating that such compositions can induce specific immunity in infectious diseases and cancer immunotherapy.

Hsps appear to induce an inflammatory reaction at the tumor site and ultimately cause a regression of the tumor burden in the cancer patients treated. Cancers which can be treated with complexes of hsps noncovalently bound to antigenic molecules include, but are not limited to, human sarcomas and carcinomas.

Accordingly, the invention provides methods of preventing and treating cancer in an individual comprising administering a composition which stimulates the immunocompetence of the host individual and elicits specific immunity against the preneoplastic and/or neoplastic cells. As used herein, "preneoplastic" cell refers to a cell which is in transition from a normal to a neoplastic form; and morphological evidence, increasingly supported by molecular biologic studies, indicates that preneoplasia progresses through multiple steps. Non-neoplastic cell growth commonly consists of hyperplasia, metaplasia, or most particularly, dysplasia (for review of such abnormal growth conditions (See Robbins and Angell, 1976, *Basic Pathology*, 2d Ed., W. B. Saunders Co., Philadelphia, pp. 68–79). Hyperplasia is a form of controlled cell proliferation involving an increase in cell number in a tissue or organ, without significant alteration in structure or function. As but one example, endometrial hyperplasia often precedes endometrial cancer. Metaplasia is a form of controlled cell growth in which one type of adult or fully differentiated cell substitutes for another type of adult cell. Metaplasia can occur in epithelial or connective tissue cells. Atypical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder. Although preneoplastic lesions may progress to neoplasia, they may also remain stable for long periods and may even regress, particularly if the inciting agent is removed or if the lesion succumbs to an immunological attack by its host.

The therapeutic regimens and pharmaceutical compositions of the invention may be used with additional immune response enhancers or biological response modifiers including, but not limited to, the cytokines IFN-α, IFN-7, IL-2, IL-4, IL-6, TNF, or other cytokine affecting immune cells. In accordance with this aspect of the invention, the complexes of the hsp and antigenic molecule are administered in combination therapy with one or more of these cytokines.

The invention further relates to administration of complexes of hsp-antigenic molecules to individuals at enhanced risk of cancer due to familial history or environmental risk factors.

5.1. Dosage Regimens

It was established in experimental tumor models (Blachere et al., 1993, *J. Immunotherapy* 14:352–356) that the lowest dose of hsp noncovalently bound to peptide complexes which produced tumor regression in mice was between 10 and 25 microgram/mouse weighing 20–25 g which is equal to 25 mg/25 g=1 mg/kg. Prior art methods extrapolate to human dosages based on body weight and surface area. For example, prior art methods of extrapolating human dosage based on body weight can be carried out as follows: since the conversion factor for converting the mouse dosage to human dosage is Dose Human per kg=Dose Mouse per kg×12 (See Freireich, E. J., et al., 1966, *Cancer Chemotherap. Rep.* 50:219–244), the effective dose of hsp-peptide complexes in humans weighing 70 kg should be 1 mg/kg÷12×70, i.e., about 6 mg (5.8 mg).

Drug doses are also given in milligrams per square meter of body surface area because this method rather than body weight achieves a good correlation to certain metabolic and excretionary functions (Shirkey, H. C., 1965, *JAMA* 193:443). Moreover, body surface area can be used as a common denominator for drug dosage in adults and children as well as in different animal species as indicated below in Table 1 (Freireich, E. J., et al., 1966, *Cancer Chemotherap. Rep.* 50:219–244).

TABLE 1

REPRESENTATIVE SURFACE AREA TO WEIGHT RATIOS (km) FOR VARIOUS SPECIES[1]

| Species | Body Weight (kg) | Surface Area (Sqm) | km Factor |
|---|---|---|---|
| Mouse | 0.02 | 0.0066 | 3.0 |
| Rat | 0.15 | 0.025 | 5.9 |
| Monkey | 3.0 | 0.24 | 12 |
| Dog | 8.0 | 0.40 | 20 |
| Human, Child | 20 | 0.80 | 25 |
| Adult | 60 | 1.6 | 37 |

Example: To express a mg/kg dose in any given species as the equivalent mg/sq m dose, multiply the dose by the appropriate km factor. In adult human, 100mg/kg is equivalent to 100 mg/kg × 37 kg/sq m = 3700 mg/sq m.
[1]Freireich, et al., 1966, Cancer Chemotherap. Rep. 50: 219–244.

In contrast to both of the above-described prior art methods of determining dosage levels, the present invention provides dosages of the purified complexes of hsps and antigenic molecules that are much smaller than the dosages estimated by the prior art. For example, according to the invention, an amount of hsp70- and/or gp96-antigenic molecule complexes is administered that is in the range of about 10 microgram to about 600 micrograms for a human patient, the preferred human dosage being the same as used in a 25 g mouse, i.e., in the range of 10–100 micrograms. The dosage for hsp-90 peptide complexes in a human patient provided by the present invention is in the range of about 50 to 5,000 micrograms, the preferred dosage being 100 micrograms.

The doses recited above are preferably given once weekly for a period of about 4–6 weeks, and the mode or site of administration is preferably varied with each administration. In a preferred example, subcutaneous administrations are given, with each site of administration varied sequentially. Thus, by way of example and not limitation, the first injection may be given subcutaneously on the left arm, the second on the right arm, the third on the left belly, the fourth on the right belly, the fifth on the left thigh, the sixth on the right thigh, etc. The same site may be repeated after a gap of one or more injections. Also, split injections may be given. Thus, for example, half the dose may be given in one site and the other half on an other site on the same day.

Alternatively, the mode of administration is sequentially varied, e.g., weekly injections are given in sequence subcutaneously, intramuscularly, intravenously or intraperitoneally.

After 4–6 weeks, further injections are preferably given at two-week intervals over a period of time of one month. Later injections may be given monthly. The pace of later injections may be modified, depending upon the patient's clinical progress and responsiveness to the immunotherapy.

The invention is illustrated by non-limiting examples in Sections 6 and 7.

5.2. Therapeutic Compositions for Immune Responses to Cancer

The compositions comprising hsp noncovalently bound to antigenic molecules are administered to elicit an effective specific immune response to the complexed antigenic molecules (and not to the hsp).

In a preferred embodiment, non-covalent complexes of hsp70, hsp90 and gp96 with peptides are prepared and purified postoperatively from tumor cells obtained from the cancer patient.

In accordance with the methods described herein, immunogenic or antigenic peptides that are endogenously complexed to hsps or MHC antigens can be used as antigenic molecules. For example, such peptides may be prepared that stimulate cytotoxic T cell responses against different tumor antigens (e.g., tyrosinase, gp100, melan-A, gp75, mucins, etc.) and viral proteins including, but not limited to, proteins of immunodeficiency virus type I (HIV-I), human immunodeficiency virus type II (HIV-II), hepatitis type A, hepatitis type B, hepatitis type C, influenza, Varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus and polio virus. In the embodiment wherein the antigenic molecules are peptides noncovalently complexed to haps in vivo, the complexes can be isolated from cells, or alternatively, produced in vitro from purified preparations each of hsps and antigenic molecules.

In another specific embodiment, antigens of cancers (e.g., tumors) or infectious agents (e.g., viral antigen, bacterial antigens, etc.) can be obtained by purification from natural sources, by chemical synthesis, or recombinantly, and, through in vitro procedures such as that described below, noncovalently complexed to hsps.

In an embodiment wherein the hsp-antigenic molecule complex to be used is a complex that is produced in vivo in cells, exemplary purification procedures such as described in Sections 5.2.1–5.2.3 below can be employed. Alternatively, in an embodiment wherein one wishes to use antigenic molecules by complexing to hsps in vitro, hsps can be purified for such use from the endogenous hsp-peptide complexes in the presence of ATP or low pH (or chemically synthesized or recombinantly produced). The protocols described herein may be used to isolate hsp-peptide complexes, or the hsps alone, from any eukaryotic cells for example, tissues, isolated cells, or immortalized eukaryote cell lines infected with a preselected intracellular pathogen, tumor cells or tumor cell lines.

5.2.1. Preparation and Purification of Hsp 70-Peptide Complexes

The purification of hsp70-peptide complexes has been described previously, see, for example, Udono et al., 1993, *Exp. Med.* 178:1391–1396. A procedure that may be used, presented by way of example but not limitation, is as follows:

Initially, tumor cells are suspended in 3 volumes of 1X Lysis buffer consisting of 5 mM sodium phosphate buffer, pH 7, 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose equilibrated with phosphate buffered saline (PBS) containing 2 mM $Ca^{2+}$ and 2 mM $Mg^{2+}$. When the cells are lysed by mechanical shearing the supernatant is diluted with an equal volume of 2× lysis buffer prior to mixing with Con A Sepharose. The supernatant is then allowed to bind to the Con A Sepharose for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC column equilibrated in 20 mM Tris-Acetate pH 7.5, 20 mM NaCl, 0.1 mM EDTA and 15 mM 2-mercaptoethanol. The column is then developed with a 20 mM to 500 mM NaCl gradient and then eluted fractions fractionated by sodium dodecyl sulfate-polyacrylamide gel electrophoresis (SDS-PAGE) and characterized by immunoblotting using an appropriate anti-hsp70 antibody (such as from clone N27F3-4, from StressGen).

Fractions strongly immunoreactive with the anti-hsp70 antibody are pooled and the hsp70-peptide complexes precipitated with ammonium sulfate; specifically with a 50%–70% ammonium sulfate cut. The resulting precipitate is then harvested by centrifugation at 17,000 rpm (SS34 Sorvall rotor) and washed with 70% ammonium sulfate. The washed precipitate is then solubilized and any residual ammonium sulfate removed by gel filtration on a Sephadex$^R$ G25 column (Pharmacia). If necessary the hsp70 preparation thus obtained can be repurified through the Mono Q FPCL Column as described above.

The hsp70-peptide complex can be purified to apparent homogeneity using this method. Typically 1 mg of hsp70-peptide complex can be purified from 1 g of cells/tissue.

The present invention further describes a new and rapid method for purification of hsp70-peptide complexes. This improved method comprises contacting cellular proteins with ADP or a nonhydrolyzable analog of ATP affixed to a solid substrate, such that hsp70 in the lysate can bind to the ADP or nonhydrolyzable ATP analog, and eluting the bound hsp70. A preferred method uses column chromatography with ADP affixed to a solid substratum (e.g., ADP-agarose). The resulting hsp70 preparations are higher in purity and devoid of contaminating peptides. The hsp70 yields are also increased significantly by about more than 10 fold. Alternatively, chromatography with nonhydrolyzable analogs of ATP, instead of ADP, can be used for purification of hsp70-peptide complexes. By way of example but not limitation, purification of hsp70-peptide complexes by ADP-agarose chromatography was carried out as described in Example Section 9.

5.2.2. Preparation and Purification of Hsp 90-Peptide Complexes

A procedure that can be used, presented by way of example and not limitation, is as follows:

Initially, tumor cells are suspended in 3 volumes of 1× Lysis buffer consisting of 5 mM sodium phosphate buffer (pH7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A Sepharose equilibrated with PBS containing 2 mM $Ca^{2+}$ and 2 mM $Mg^{2+}$. When the cells are lysed by mechanical shearing the supernatant is diluted with an equal volume of 2× Lysis buffer prior to mixing with Con A Sepharose. The supernatant is then allowed to bind to the Con A Sepharose for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a Mono Q FPLC column equilibrated with lysis buffer. The proteins are then eluted with a salt gradient of 200 mM to 600 mM NaCl.

The eluted fractions are fractionated by SDS-PAGE and fractions containing the hsp90-peptide complexes identified by immunoblotting using an anti-hsp90 antibody such as 3G3 (Affinity Bioreagents). Hsp90-peptide complexes can be purified to apparent homogeneity using this procedure. Typically, 150–200 μg of hsp90-peptide complex can be purified from 1 g of cells/tissue.

5.2.3. Preparation and Purification of gp96-Peptide Complexes

A procedure that can be used, presented by way of example and not limitation, is as follows:

A pellet of tumors is resuspended in 3 volumes of buffer consisting of 30 mM sodium bicarbonate buffer (pH 7.5) and 1 mM PMSF and the cells allowed to swell on ice 20 minutes. The cell pellet then is homogenized in a Dounce homogenizer (the appropriate clearance of the homogenizer will vary according to each cells type) on ice until >95% cells are lysed.

The lysate is centrifuged at 1,000 g for 10 minutes to remove unbroken cells, nuclei and other debris. The supernatant from this centrifugation step then is recentrifuged at 100,000 g for 90 minutes. The gp96-peptide complex can be purified either from the 100,000 pellet or from the supernatant.

When purified from the supernatant, the supernatant is diluted with equal volume of 2× lysis buffer and the supernatant mixed for 2–3 hours at 4° C. with Con a sepharose equilibrated with PBS containing 2 mM $Ca^{2+}$ and 2 mM $Mg^{2+}$. Then, the slurry is packed into a column and washed with 1× lysis buffer until the $OD_{280}$ drops to baseline. Then, the column is washed with ⅓ column bed volume of 10% α-methyl mannoside (α-MM) dissolved in PBS containing 2 mM $Ca^{2+}$ and 2 mM $Mg^{2+}$, the column sealed with a piece of parafilm, and incubated at 37° C. for 15 minutes. Then the column is cooled to room temperature and the parafilm removed from the bottom of the column. Five column volumes of the α-MM buffer are applied to the column and the eluate analyzed by SDS-PAGE. Typically the resulting material is about 60–95% pure, however this depends upon the cell type and the tissue-to-lysis buffer ratio used. Then the sample is applied to a Mono Q FPLC column (Pharmacia) equilibrated with a buffer containing 5 mM sodium phosphate, pH 7. The proteins then are eluted from the column with a 0–1M NaCl gradient and the gp96 fraction elutes between 400 mM and 550 mM NaCl.

The procedure, however, may be modified by two additional steps, used either alone or in combination, to consistently produce apparently homogeneous gp96-peptide complexes. One optional step involves an ammonium sulfate precipitation prior to the Con A purification step and the other optional step involves DEAE-Sepharose purification after the Con A purification step but before the Mono Q FPLC step.

In the first optional step, the supernatant resulting from the 100,000g centrifugation step is brought to a final concentration of 50% ammonium sulfate by the addition of ammonium sulfate. The ammonium sulfate is added slowly while gently stirring the solution in a beaker placed in a tray of ice water. The solution is stirred from about ½ to 12 hours at 4*C and the resulting solution centrifuged at 6,000 rpm (Sorvall SS34 rotor). The supernatant resulting from this step is removed, brought to 70% ammonium sulfate saturation by the addition of ammonium sulfate solution, and centrifuged at 6,000 rpm (Sorvall SS34 rotor). The resulting pellet from this step is harvested and suspended in PBS containing 70% ammonium sulfate in order to rinse the pellet. This mixture is centrifuged at 6,000 rpm (Sorvall SS34 rotor) and the pellet dissolved in PBS containing 2 mM $Ca^{2+}$ and $Mg^{2+}$. Undissolved material is removed by a brief centrifugation at 15,000 rpm (Sorvall SS34 rotor). Then, the solution is mixed with Con A Sepharose and the procedure followed as before.

In the second optional step, the gp96 containing fractions eluted from the Con A column are pooled and the buffer exchanged for 5 mM sodium phosphate buffer, pH 7, 300 mM NaCl by dialysis, or preferably by buffer exchange on a Sephadex G25 column. After buffer exchange, the solution is mixed with DEAE-Sepharose previously equilibrated with 5 mM sodium phosphate buffer, pH 7, 300 mM NaCl. The protein solution and the beads are mixed gently for 1 hour and poured into a column. Then, the column is washed with 5SM sodium phosphate buffer, pH 7, 300 mM NaCl, until the absorbance at 280 nM drops to baseline. Then, the bound protein is eluted from the column with five volumes of 5 mM sodium phosphate buffer, pH 7, 700 mM NaCl. Protein containing fractions are pooled and diluted with 5 mM sodium phosphate buffer, pH 7 in order to lower the salt concentration to 175 mM. The resulting material then is applied to the Mono Q FPLC column (Pharmacia) equilibrated with 5 mM sodium phosphate buffer, pH 7 and the protein that binds to the Mono Q FPLC column (Pharmacia) is eluted as described before.

It is appreciated, however, that one skilled in the art may assess, by routine experimentation, the benefit of incorporating the second optional step into the purification protocol. In addition, it is appreciated also that the benefit of adding each of the optional steps will depend upon the source of the starting material.

When the gp96 fraction is isolated from the 100,000 g pellet, the pellet is suspended in 5 volumes of PBS containing either 1% sodium deoxycholate or 1% octyl glucopyranoside (but without the $Mg^{2+}$ and $Ca^{2+}$) and incubated on ice for 1 hour. The suspension is centrifuged at 20,000 g for 30 minutes and the resulting supernatant dialyzed against several changes of PBS (also without the $Mg^{2+}$ and $Ca^{2+}$) to remove the detergent. The dialysate is centrifuged at 100,000 g for 90 minutes, the supernatant harvested, and calcium and magnesium are added to the supernatant to give final concentrations of 2 mM, respectively. Then the sample is purified by either the unmodified or the modified method for isolating gp96-peptide complex from the 100,000 g supernatant, see above.

The gp96-peptide complexes can be purified to apparent homogeneity using this procedure. About 10–20 μg of gp96 can be isolated from 1 g cells/tissue.

Infectious Disease

In an alternative embodiment wherein it is desired to treat a patient having an infectious disease the above-described methods in Sections 5.2.1–5.2.3 are used to isolate hsp-peptide complexes from cells infected with an infectious organism, e.g., of a cell line or from a patient. Such infectious organisms include but are not limited to, viruses, bacterial, protozoa, fungi, and parasites as described in detail in Section 5.2.4 below.

5.2.4. Isolation of Antigenic/Immunogenic Components

It has been found that antigenic peptides and/or components can be eluted from hsp-complexes either in the presence of ATP or low pH. These experimental conditions may be used to isolate peptides and/or antigenic components from cells which may contain potentially useful antigenic determinants. Once isolated, the amino acid sequence of each antigenic peptide may be determined using conventional amino acid sequencing methodologies. Such antigenic molecules can then be produced by chemical synthesis or recombinant methods, purified, and complexed to hsps in vitro.

Similarly, it has been found that potentially immunogenic peptides may be eluted from MHC-peptide complexes using techniques well know in the art (Falk, K. et al., 1990 *Nature* 348:248–251; Elliott, T., et al., 1990, *Nature* 348:195–197; Falk, K., et al., 1991, *Nature* 351:290–296).

Thus, potentially immunogenic or antigenic peptides may be isolated from either endogenous stress protein-peptide complexes or endogenous MHC-peptide complexes for use subsequently as antigenic molecules, by complexing in vitro to hops. Exemplary protocols for isolating peptides and/or antigenic components from either of the these complexes are set forth below in Sections 5.2.4.1 and 5.2.4.2.

5.2.4.1 Peptides From Stress Protein-Peptide Complexes

Two methods may be used to elute the peptide from a stress protein-peptide complex. One approach involves incubating the stress protein-peptide complex in the presence of ATP. The other approach involves incubating the complexes in a low pH buffer.

Briefly the complex of interest is centrifuged through a Centricon 10 assembly (Millipore) to remove any low molecular weight material loosely associated with the complex. The large molecular weight fraction may be removed and analyzed by SDS-PAGE while the low molecular weight may be analyzed by HPLC as described below. In the ATP incubation protocol, the stress protein-peptide complex in the large molecular weight fraction is incubated with 10 mM ATP for 30 minutes at room temperature. In the low pH protocol, acetic acid or trifluoroacetic acid is added to the stress protein-peptide complex to give a final concentration of 10% (vol/vol) and the mixture incubated at room temperature or in a boiling water bath or any temperature in between, for 10 minutes (See, Van Bleek, et al., 1990, *Nature* 348:213–216; and Li, et al., 1993, *EMBO Journal* 12:3143–3151).

The resulting samples are centrifuged through an Centricon 10 assembly as mentioned previously. The high and low molecular weight fractions are recovered. The remaining large molecular weight stress protein-peptide complexes can be reincubated with ATP or low pH to remove any remaining peptides.

The resulting lower molecular weight fractions are pooled, concentrated by evaporation and dissolved in 0.1% trifluoroacetic acid (TFA). The dissolved material is then fractionated by reverse phase high pressure liquid chromatography (HPLC) using for example a VYDAC™ (Separations Group, Inc., Hesperia, Calif.) CIB reverse phase column equilibrated with 0.1% TFA. The bound material is then eluted at a flow rate of about 0.8 ml/min by developing the column with a linear gradient of 0 to 80% acetonitrile in 0.1% TFA. The elution of the peptides can be monitored by $OD_{210}$ and the fractions containing the peptides collected.

5.2.4.2 Peptides from MHC-Peptide Complexes

The isolation of potentially immunogenic peptides from MHC molecules is well known in the art and so is not described in detail herein (See, Falk, et al., 1990, *Nature* 348:248–251; Rotzsche, at al., 1990, *Nature* 348:252–254; Elliott, et al., 1990, *Nature* 348:191–197; Falk, et al., 1991, *Nature* 351:290–296; Demotz, et al., 1989, *Nature* 343:682–684; Rotzsche, et al., 1990, *Science* 249:283–287), the disclosures of which are incorporated herein by reference.

Briefly, MHC-peptide complexes may be isolated by a conventional immunoaffinity procedure. The peptides then may be eluted from the MHC-peptide complex by incubating the complexes in the presence of about 0.1% TFA in acetonitrile. The eluted peptides may be fractionated and purified by reverse phase HPLC, as before.

The amino acid sequences of the eluted peptides may be determined either by manual or automated amino acid sequencing techniques well known in the art. Once the amino acid sequence of a potentially protective peptide has been determined the peptide may be synthesized in any desired amount using conventional peptide synthesis or other protocols well known in the art.

Peptides having the same amino acid sequence as those isolated above may be synthesized by solid-phase peptide synthesis using procedures similar to those described by Merrifield, 1963, *J. Am. Chem. Soc.*, 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free-amino group to the activated carboxyl leads to peptide bond formation. The most commonly used N-α-protecting groups include Boc which is acid labile and Fmoc which is base labile.

Briefly, the C-terminal N-α-protected amino acid is first attached to the polystyrene beads. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton, et al., 1989, *Solid Phase Peptide Synthesis: A Practical Approach,* IRL Press, and Bodanszky, 1993, *Peptide Chemistry, A Practical Textbook,* 2nd Ed., Springer-Verlag).

Purification of the resulting peptides is accomplished using conventional procedures, such as preparative HPLC using gel permeation, partition and/or ion exchange chromatography. The choice of appropriate matrices and buffers are well known in the art and so are not described in detail herein.

5.2.5 Exogenous Antigenic Molecules

Antigens or antigenic portions thereof can be selected for use as antigenic molecules, for complexing to hsps, from among those known in the art or determined by immunoassay to be able to bind to antibody or MHC molecules (antigenicity) or generate immune response (immunogenicity). To determine immunogenicity or antigenicity by detecting binding to antibody, various immunoassays known in the art can be used, including but not limited to competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in vivo immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are envisioned for use. In one embodiment for detecting immuogenicity, T cell-mediated responses can be assayed by standard methods, e.g., in vitro cytoxicity assays or in vivo delayed-type hypersensitivity assays.

Potentially useful antigens or derivatives thereof for use as antigenic molecules can also be identified by various criteria, such as the antigen's involvement in neutralization of a pathogen's infectivity (wherein it is desired to treat or prevent infection by such a pathogen) (Norrby, 1985, *Summary,* in Vaccines 85, Lerner, et al. (eds.), Cold Spring Harbor Laboratory, Cold Spring Harbor, N.Y., pp. 388–389), type or group specificity, recognition by patients antisera or immune cells, and/or the demonstration of protective effects of antisera or immune cells specific for the antigen. In addition, where it is desired to treat or prevent a disease caused by pathogen, the antigen's encoded epitope should preferably display a small or no degree of antigenic variation in time or amongst different isolates of the same pathogen.

Preferably, where it is desired to treat or prevent cancer, known tumor-specific antigens or fragments or derivatives thereof are used. For example, such tumor specific or tumor-associated antigens include but are not limited to KS ¼ pan-carcinoma antigen (Perez and Walker, 1990, *J. Immunol.* 142:3662–3667; Bumal, 1988, *Hybridoma* 7(4):407–415); ovarian carcinoma antigen (CA125) (Yu, et al., 1991, *Cancer Res.* 51(2):468–475); prostatic acid phosphate (Tailer, et al., 1990, *Nucl. Acids Res.* 18(16):4928); prostate specific antigen (Henttu and Vihko, 1989, *Biochem. Biophys. Res. Comm.* 160(2):903–910; Israeli, et al., 1993, *Cancer Res.* 53:227–230); melanoma-associated antigen p97 (Estin, et al., 1989, *J. Natl. Cancer Inst.* 81(6):445–446); melanoma antigen gp75 (Vijayasardahl, et al., 1990, *J. Exp. Med.* 171(4):1375–1380); high molecular weight melanoma antigen (Natali, et al., 1987, *Cancer* 59:55–63) and prostate specific membrane antigen.

In a specific embodiment, an antigen or fragment or derivative thereof specific to a certain tumor is selected for complexing to hsp and subsequent administration to a patient having that tumor.

Preferably, where it is desired to treat or prevent viral diseases, molecules comprising epitopes of known viruses are used. For example, such antigenic epitopes may be prepared from viruses including, but not limited to, hepatitis type A hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, human immunodeficiency virus type I (HIV-I), and human immunodeficiency virus type II (HIV-II).

Preferably, where it is desired to treat or prevent bacterial infections, molecules comprising epitopes of known bacteria are used. For example, such antigenic epitopes may be prepared from bacteria including, but not limited to, mycobacteria rickettsia, mycoplasma, neisseria and legionella.

Preferably, where it is desired to treat or prevent protozoal infectious, molecules comprising epitopes of known protozoa are used. For example, such antigenic epitopes may be prepared from protozoa including, but not limited to, leishmania, kokzidioa, and trypanosoma.

Preferably, where it is desired to treat or prevent parasitic infectious, molecules comprising epitopes of known parasites are used. For example, such antigenic epitopes may be from parasites including, but not limited to, chlamydia and rickettsia.

5.2.6 In Vitro Production of Stress Protein-Antigenic Molecule Complexes

In an embodiment in which complexes of hsps and the peptides with which they are endogenously associated in vivo are not employed, complexes of hsps to antigenic molecules are produced in vitro. As will be appreciated by those skilled in the art, the peptides either isolated by the aforementioned procedures or chemically synthesized or recombinantly produced may be reconstituted with a variety of naturally purified or recombinant stress proteins in vitro to generate immunogenic non-covalent stress protein-antigenic molecule complexes. Alternatively, exogenous antigens or antigenic/immunogenic fragments or derivatives thereof can be noncovalently complexed to stress proteins for use in the immunotherapeutic or prophylactic vaccines of the invention. A preferred, exemplary protocol for noncovalently complexing a stress protein and an antigenic molecule in vitro is discussed below.

Prior to complexing, the hsps are pretreated with ATP or low pH to remove any peptides that may be associated with the hsp of interest. When the ATP procedure is used, excess ATP is removed from the preparation by the addition of apyranase as described by Levy, et al., 1991, *Cell* 67:265–274. When the low pH procedure is used, the buffer is readjusted to neutral pH by the addition of pH modifying reagents.

The antigenic molecules (log) and the pretreated hsp (9 $\mu$g) are admixed to give an approximately 5 antigenic molecule: 1 stress protein molar ratio. Then, the mixture is incubated for 15 minutes to 3 hours at 40 to 45° C. in a suitable binding buffer such as one containing 20 mM sodium phosphate, pH 7.2, 350 mM NaCl, 3 mM $MgCl_2$ and 1 mM phenyl methyl sulfonyl fluoride (PMSF). The preparations are centrifuged through Centricon 10 assembly (Millipore) to remove any unbound peptide. The association of the peptides with the stress proteins can be assayed by SDS-PAGE. This is the preferred method for in vitro complexing of peptides isolated from MHC-peptide complexes of peptides disassociated from endogenous hsp-peptide complexes.

In an alternative embodiment of the invention, preferred for producing complexes of hsp70 to exogenous antigenic molecules such as proteins, 5–10 micrograms of purified hsp is incubated with equimolar quantities of the antigenic molecule in 20 mM sodium phosphate buffer pH 7.5, 0.5M NaCl, 3 mM $MgCl_2$ and 1 mM ADP in a volume of 100 microliter at 37° C. for 1 hr. This incubation mixture is further diluted to 1 ml in phosphate-buffered saline.

In an alternative embodiment of the invention, preferred for producing complexes of gp96 or hsp90 to peptides, 5–10 micrograms of purified gp96 or hsp90 is incubated with equimolar or excess quantities of the antigenic peptide in a suitable buffer such as one containing 20 mM sodium phosphate buffer pH 7.5, 0.5M NaCl, 3 nM $MgCl_2$ at 60–65° C. for 5–20 min. This incubation mixture is allowed to cool to room temperature and centrifuged one or more times if necessary, through Centricon 10 assembly (Millipore) to remove any unbound peptide.

Following complexing, the immunogenic stress protein-antigenic molecule complexes can optionally be assayed in vitro using for example the mixed lymphocyte tumor cell assay (MLTC) described below. Once immunogenic complexes have been isolated they can be optionally characterized further in animal models using the preferred administration protocols and excipients discussed below.

5.2.7 Determination of Immunogenicity of Stress Protein-Peptide Complexes

The purified stress protein-antigenic molecule complexes can be assayed for immunogenicity using the mixed lymphocyte tumor culture assay (MLTC) well known in the art.

By way of example but not limitation, the following procedure can be used. Briefly, mice are injected subcutaneously with the candidate stress protein-antigenic molecule complexes. Other mice are injected with either other stress protein peptide complexes or whole infected cells which act as positive controls for the assay. The mice are injected twice, 7–10 days apart. Ten days after the last immunization, the spleens are removed and the lymphocytes released. The released lymphocytes may be restimulated subsequently in vitro by the addition of dead cells that express d the complex of interest.

For example, $8 \times 10^6$ immune spleen cells may be stimulated with $4 \times 10^4$ mitomycin C treated or $\gamma$-irradiated (5–10, 000 rads) infected cells (or cells transfected with an appropriate gene, as the case may be) in 3 ml RPMI medium containing 10% fetal calf serum. In certain cases 334 secondary mixed lymphocyte culture supernatant may be included in the culture medium as a source of T cell growth factors (See, Glasebrook, et al., 1980, *J. Exp. Med.* 151:876). To test the primary cytotoxic T cell response after immunization, spleen cells may be cultured without stimulation. In some experiments spleen cells of the immunized mice may also be restimulated with antigenically distinct cells, to determine the specificity of the cytotoxic T cell response.

Six days later the cultures are tested for cytotoxicity in a 4 hour $^{51}$Cr-release assay (See, Palladino, et al., 1987, *Cancer Res.* 47:5074–5079 and Blachere, at al., 1993, *J. Immunotherapy* 14:352–356). In this assay, the mixed lymphocyte culture is added to a target cell suspension to give different effector:target (E:T) ratios (usually 1:1 to 40:1). The target cells are prelabelled by incubating 1×10$^6$ target cells in culture medium containing 200 mCi $^{51}$Cr/ml for one hour at 37° C. The cells are washed three times following labeling. Each assay point (E:T ratio) is performed in triplicate and the appropriate controls incorporated to measure spontaneous $^{51}$Cr release (no lymphocytes added to assay) and 100% release (cells lysed with detergent). After incubating the cell mixtures for 4 hours, the cells are pelleted by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm.

In order to block the MHC class I cascade a concentrated hybridoma-supernatant derived from K-44 hybridoma cells (an anti-MHC class I hybridoma) is added to the test samples to a final-concentration of 12.5%.

5.3. Formulation

Hsp-antigenic molecule complexes of the invention may be formulated into pharmaceutical preparations for administration to mammals for treatment or prevention of cancer or infectious diseases. Compositions comprising a compound of the invention formulated in a compatible pharmaceutical carrier may be prepared, packaged, and labelled for treatment of the indicated tumor, such as human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. Alternatively, it can be labeled for treatment of the appropriate infectious diseases Alternatively, pharmaceutical compositions may be formulated for treatment of appropriate infectious diseases.

If the complex is water-soluble, then it may be formulated in an appropriate buffer, for example, phosphate buffered saline or other physiologically compatible solutions. Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The pharmaceutical compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically or prophylactically effective amounts of the hsp-antigenic molecule complexes in pharmaceutically acceptable form. The hsp-antigenic molecule complex in a vial of a kit of the invention may be in the form of a pharmaceutically acceptable solution, e.g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e.g., saline, dextrose solution, etc.), preferably sterile, to reconstitute the complex to form a solution for is injection purposes.

In another embodiment, a kit of the invention further comprises a needle or syringe, preferably packaged in sterile form, for injecting the complex, and/or a packaged alcohol pad. Instructions are optionally included for administration of hsp-antigenic molecule complexes by a clinician or by the patient.

5.4 Target Infectious Diseases

Infectious diseases that can be treated or prevented by the methods of the present invention are caused by infectious agents including, but not limited to, viruses, bacteria, fungi, protozoa and parasites.

Viral diseases that can be treated or prevented by the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, human immunodeficiency virus type I (HIV-I), and human immunodeficiency virus type II (HIV-II).

Bacterial diseases that can be treated or prevented by the methods of the present invention are caused by bacteria including, but not limited to, mycobacteria rickettsia, mycoplasma, neisseria and legionella.

Protozoal diseases that can be treated or prevented by the methods of the present invention are caused by protozoa including, but not limited to, leishmania, kokzidioa, and trypanosoma.

Parasitic diseases that can be treated or prevented by the methods of the present invention are caused by parasites including, but not limited to, chlamydia and rickettsia.

5.5. Target Cancers

Cancers that can be treated or prevented by the methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrdm's macroglobulinemia, and heavy chain disease. Specific examples of such cancers are described in the sections below.

In a specific embodiment the cancer is metastatic. In another specific embodiment, the patient having a cancer is immunosuppressed by reason of having undergone anti-cancer therapy (e.g., chemotherapy radiation) prior to administration of the hsp-antigenic molecule complexes of the invention.

5.5.1. Colorectal Cancer Metastatic to the Liver

In 1992, approximately 150,000 Americans were diagnosed with colorectal cancer and more than 60,000 died as a result of colorectal metastases. At the time of their deaths, 80 percent of patients with colorectal cancer have metastatic disease involving the liver, and one-half of these patients have no evidence of other (extrahepatic) metastases. Most metastatic tumors of the liver are from gastrointestinal primaries. Unfortunately, the natural history of metastatic liver lesions carries a grave prognosis and systemic chemotherapy regimens have been unable to induce significant response rates or alter length of survival (Drebin, J. A., et al., in *Current Therapy In Oncology*, ed. J. E. Niederhuber, B. C. Decker, Mosby, 1993, p.426).

Colorectal cancer initially spreads to regional lymph nodes and then through the portal venous circulation to the liver, which represents the most common visceral site of metastasis. The symptoms that lead patients with colorectal cancer to seek medical care vary with the anatomical location of the lesion. For example, lesions in the ascending colon frequency ulcerate, which leads to chronic blood loss in the stool.

Radical resection offers the greatest potential for cure in patients with invasive colorectal cancer. Before surgery, the CEA titer is determined. Radiation therapy and chemotherapy are used in patients with advanced colorectal cancer. Results with chemotherapeutic agents (e.g., 5-fluorouracil) are mixed and fewer than 25 percent of patients experience a greater than 50 percent reduction in tumor mass (Richards, 2d., F., et al., 1986, *J. Clin. Oncol.* 4:565).

Patients with widespread metastases have limited survival and systemic chemotherapy has little impact in this group of patients. In addition, systemically administered chemotherapy is often limited by the severity of toxicities associated with the various agents, such as severe diarrhea, mucositis and/or myelosuppression. Other techniques, including hepatic radiation, systemic chemotherapy, hepatic arterial ligation, tumor embolization and immunotherapy have all been explored, but, for the most part, have proven ineffectual in prolonging patient survival.

In a specific embodiment, the present invention provides compositions and methods for enhancing tumor specific immunity in individuals suffering from colorectal cancer metastasized to the liver, in order to inhibit the progression of the neoplastic disease. Preferred methods of treating these neoplastic diseases comprise administering a composition of autologous hsp noncovalently bound to peptide complexes, which elicits tumor-specific immunity against the tumor cells. Most specifically, the use of a composition of the invention, comprising gp96, can result in nearly complete inhibition of liver cancer growth in cancer patients, without inducing toxicity and thus providing a dramatic therapeutic effect.

Accordingly, as an example of the method of the invention, gp96 is administered to a patient diagnosed with colorectal cancer, with or without liver metastasis, via one of many different routes of administration, the preferred routes being subcutaneous at different anatomical sites, e.g., left arm, right arm, left belly, right belly, left thigh, right thigh, etc. These routes of administration are used in sequence and the site of injection is varied for each weekly injection as described in Section 7. The preparations and use of therapeutically effective compositions for the prevention and treatment of primary and metastatic cancers are described in detail in the sections which follow and by way of example, infra.

5.5.2. Hepatocellular Carcinoma

Hepatocellular carcinoma is generally a disease of the elderly in the United States. Although many factors may lead to hepatocellular carcinoma, the disease is usually limited to those persons with preexisting liver disease. Approximately 60 to 80 percent of patients in the United States with hepatocellular carcinoma have a cirrhotic liver and about four percent of individuals with a cirrhotic liver eventually develop hepatocellular carcinoma (Niederhuber, J. E., (ed.), 1993, *Current Therapy in Oncology,* B. C. Decker, Mosby). The risk is highest in patients whose liver disease is caused by inherited hemochromatosis or hepatic B viral infection (Bradbear, R. A., et al., 1985, *J. Natl. Cancer Inst.* 75:81; Beasley, R. P., et al., 1981, *Lancet* 2:1129). Other causes of cirrhosis that can lead to hepatocellular carcinoma include alcohol abuse and hepatic fibrosis caused by chronic administration of methotrexate. The most frequent symptoms of hepatocellular carcinoma are the development of a painful mass in the right upper quadrant or epigastrium, accompanied by weight loss. In patients with cirrhosis, the development of hepatocellular carcinoma is preceded by ascites, portal hypertension and relatively abrupt clinical deterioration. In most cases, abnormal values in standard liver function tests such as serum aminotransferase and alkaline phosphatase are observed.

CT scans of the liver are used to determine the anatomic distribution of hepatocellular carcinoma and also provide orientation for percutaneous needle biopsy. Approximately 70 percent of patients with hepatocellular carcinoma have an elevated serum alpha-fetoprotein concentration (McIntire, K. R., at al., 1975, *Cancer Res.* 35:991) and its concentration correlates with the extent of the disease.

Radical resection offers the only hope for cure in S patients with hepatocellular carcinoma. Such operative procedures are associated with five-year survival rates of 12 to 30 percent. Liver transplantation may improve survival of some younger individuals. However, most patients are not surgical candidates because of extensive cirrhosis multifocal tumor pattern or scarcity of compatible donor organs. Chemotherapeutic agents have been administered either by intravenous route or through an intrahepatic arterial catheter. Such therapy has sometimes been combined with irradiation to the liver. Reductions in the size of measurable tumors of 50% or more have been reported in some patients treated with either systemic doxorubicin or 5-fluorouracil. However, chemotherapy often induces immunosuppression and rarely causes the tumor to disappear completely and the duration of response is short. The prognosis for patients with hepatocellular carcinoma is negatively correlated with cirrhosis and metastases to the lungs or bone. Median survival for patients is only four to six months. In another specific embodiment, the present invention provides compositions and methods for enhancing specific immunity in individuals suffering from hepatocellular carcinoma in order to inhibit the progression of the neoplastic disease and ultimately eradicate all preneoplastic and neoplastic cells.

5.5.3. Breast Cancer

Another specific aspect of the invention relates to the treatment of breast cancer. The American Cancer Society estimated that in 1992 180,000 American women were diagnosed with breast cancer and 46,000 succumbed to the disease (Niederhuber, J. E. ed. *Current Therapy in Oncology* B. C. Decker, Mosby, 1993). This makes breast cancer the second major cause of cancer death in women, ranking just behind lung cancer. A disturbing fact is the observation that breast cancer has been increasing at a rate of 3 percent per year since 1980 (Niederhuber, J. E., ed. *Current Therapy in Oncology,* B. C. Decker, Mosby, (1993)). The treatment of breast cancer presently involves surgery, radiation, hormonal therapy and/or chemotherapy. Consideration of two breast cancer characteristics, hormone receptors and disease extent, has governed how hormonal therapies and standard-dose chemotherapy are sequenced to improve survival and maintain or improve quality of life. A wide range of multi-drug regimens have been used as adjuvant therapy in breast cancer patients, including, but not limited to combinations of 2 cyclophosphamide, doxorubicin, vincristine methotrexate, 5-fluorouracil and/or leucovorin. In a specific embodiment, the present invention provides hsp compositions and methods for enhancing specific immunity to preneoplastic and neoplastic mammary cells in women. The present invention also provides compositions and methods for preventing the development of neoplastic cells in women at enhanced risk for breast cancer, and for inhibiting cancer cell proliferation and metastasis. These compositions can be applied alone or in combination with each other or with biological response modifiers.

5.6. Autologous Embodiment

The specific immunogenicity of hsps derives not from hsps per se, but from the peptides bound to them. In a preferred embodiment of the invention directed to the use of autologous complexes of hsp-peptides as cancer vaccines, two of the most intractable hurdles to cancer immunotherapy are circumvented. First is the possibility that human cancers, like cancers of experimental animals, are antigenically distinct. In an embodiment of the present invention, hsps chaperone antigenic peptides of the cancer cells from which they are derived and circumvent this hurdle. Second, most current approaches to cancer immunotherapy focus on determining the CTL-recognized epitopes of cancer cell lines. This approach requires the availability of cell lines and CTLs against cancers. These reagents are unavailable for an overwhelming proportion of human cancers. In an embodiment of the present invention directed to autologous complexes of hsps and peptides, cancer immunotherapy does not depend on the availability of cell lines or CTLs nor does it require definition of the antigenic epitopes of cancer cells. These advantages make autologous hsps noncovalently bound to peptide complexes attractive and novel immunogens against cancer.

5.7. Prevention and Treatment of Primary and Metastatic Neoplastic Diseases

There are many reasons why immunotherapy as provided by the present invention is desired for use in cancer patients. First, if cancer patients are immunosuppressed and surgery, with anesthesia, and subsequent chemotherapy, may worsen the immunosuppression, then with appropriate immunotherapy in the preoperative period, this immunosuppression may be prevented or reversed. This could lead to fewer infectious complications and to accelerated wound healing. Second, tumor bulk is minimal following surgery and immunotherapy is most likely to be effective in this situation. A third reason is the possibility that tumor cells are shed into the circulation at surgery and effective immunotherapy applied at this time can eliminate these cells.

The preventive and therapeutic methods of the invention are directed at enhancing the immunocompetence of the cancer patient either before surgery, at or after surgery, and to induce tumor-specific immunity to cancer cells, with the objective being inhibition of cancer, and with the ultimate clinical objective being total cancer regression and eradication.

5.8. Monitoring of Effects During Cancer Prevention and Immunotherapy with Hsp-peptide Complexes The effect of immunotherapy with hsp-antigenic molecule complexes on development and progression of neoplastic diseases can be monitored by any methods known to one skilled in the art, including but not limited to measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology of tumors using techniques such as a computed tomographic (CT) scan; and e) changes in levels of putative biomarkers of risk for a particular cancer in individuals at high risk, and f) changes in the morphology of tumors using a sonogram.

5.8.1. Delayed Hypersensitivity Skin Test

Delayed hypersensitivity skin tests are of great value in the overall immunocompetence and cellular immunity to an antigen. Inability to react to a battery of common skin antigens is termed anergy (Sato, T., et al, 1995, *Clin. Immunol. Pathol.* 74:35–43).

Proper technique of skin testing requires that the antigens be stored sterile at 4° C., protected from light and reconstituted shortly before use. A 25- or 27-gauge needle ensures intradermal, rather than subcutaneous, administration of antigen. Twenty-four and 48 hours after intradermal administration of the antigen, the largest dimensions of both erythema and induration are measured with a ruler. Hypoactivity to any given antigen or group of antigens is confirmed by testing with higher concentrations of antigen or, in ambiguous circumstances, by a repeat test with an intermediate concentration.

5.8.2. Activity of Cytolytic T-lymphocytes In Vitro $8 \times 10^6$ Peripheral blood derived T lymphocytes isolated by the Ficoll-Hypaque centrifugation gradient technique, are restimulated with $4 \times 10^4$ mitomycin C treated tumor cells in 3 ml RPMI medium containing 10% fetal calf serum. In some experiments, 33% secondary mixed lymphocyte culture supernatant or IL-2, is included in the culture medium as a source of T cell growth factors.

In order to measure the primary response of cytolytic T-lymphocytes after immunization, T cells are cultured without the stimulator tumor cells. In other experiments, T cells are restimulated with antigenically distinct cells. After six days, the cultures are tested for cytotoxity in a 4 hour $^{51}$Cr-release assay. The spontaneous $^{51}$Cr-release of the targets should reach a level less than 20%. For the anti-MHC class I blocking activity, a tenfold concentrated supernatant of W6/32 hybridoma is added to the test at a final concentration of 12.5% (Heike M., et al., *J. Immunotherapy* 15:165–174).

5.8.3. Levels of Tumor Specific Antigens

Although it may not be possible to detect unique tumor antigens on all tumors, many tumors display antigens that distinguish them from normal cells. The monoclonal antibody reagents have permitted the isolation and biochemical characterization of the antigens and have been invaluable diagnostically for distinction of transformed from nontransformed cells and for definition of the cell lineage of transformed cells. The best-characterized human tumor-associated antigens are the oncofetal antigens. These antigens are expressed during embryogenesis, but are absent or very difficult to detect in normal adult tissue. The prototype antigen is carcinoembryonic antigen (CEA), a glycoprotein found on fetal gut an human colon cancer cells, but not on normal adult colon cells. Since CEA is shed from colon carcinoma cells and found in the serum, it was originally thought that the presence of this antigen in the serum could be used to screen patients for colon cancer. However, patients with other tumors, such as pancreatic and breast cancer, also have elevated serum levels of CEA. Therefore, monitoring the fall and rise of CEA levels in cancer patients undergoing therapy has proven useful for predicting tumor progression and responses to treatment.

Several other oncofetal antigens have been useful for diagnosing and monitoring human tumors, e.g., alpha-fetoprotein, an alpha-globulin normally secreted by fetal liver and yolk sac cells, is found in the serum of patients with liver and germinal cell tumors and can be used as a matter of disease status.

5.8.4. Computed Tomographic (CT) Scan

CT remains the choice of techniques for the accurate staging of cancers. CT has proved more sensitive and specific than any other imaging techniques for the detection of metastases.

5.8.5. Measurement of Putative Biomarkers

The levels of a putative biomarker for risk of a specific cancer are measured to monitor the effect of hsp noncovalently bound to peptide complexes. For example, in individuals at enhanced risk for prostate cancer, serum prostate-specific antigen (PSA) is measured by the procedure described by Brawer, M. K., et. al., 1992, *J. Urol.* 147:841–845, and Catalona, W. J., et al., 1993, *JAMA* 270:948–958; or in individuals at risk for colorectal cancer CEA is measured as described above in Section 4.5.3; and in individuals at enhanced risk for breast cancer, 16-α-hydroxylation of estradiol is measured by the procedure described by Schneider, J. et al., 1982, Proc. Natl. Acad. Sci. ISA 79:3047–3051. The references cited above are incorporated by reference herein in their entirety.

5.8.6. Sonogram

A Sonogram remains an alternative choice of technique for the accurate staging of cancers.

6. EXAMPLE

Administration of Hsp-Peptide Complexes in two UV-Induced Carcinoma Models in Mice a) Tumor models:

Two UV-induced carcinomas were studied in the C3H/HeN mice (Ward, et al., 1989, *J. Exp. Med.* 170:217): (i) the highly immunogenic UV6138 carcinoma, and (ii) the less immunogenic UV6139SJ carcinoma.

b) Gp96 preparations were prepared from the UV6138 and UV6139SJ carcinomas by the procedures described above in Section 5.2.3. The gp96 preparations were administered without adjuvants.

6.1 Prevention Modality a) Materials and Method:

The ability of gp96 preparations to prevent development of UV-induced carcinoma was tested. A total of six groups of female $C_3H/HeN$ mice (obtained from the National Cancer Institute, Frederick, Md.), weighing approximately 25 g each, were used. Two groups of mice were given twice at a ten day interval, either (i) phosphate buffer saline (PBS), (ii) 25 microgram/mouse of gp96 derived from UV6138 carcinomas, or (iii) 25 microgram/mouse of gp96 derived from UV3169SJ carcinoma.

In each set, mice were challenged with $10^7$ cells from either the UV6138 carcinoma or the UV6139SJ carcinoma 15 days after the second injection with PBS or gp96. Tumors were measured at 2 day intervals. Since the UV6138 tumor is a regressor tumor, mice were irradiated at 400 rad 10 days after the second injection with PBS or gp96 in order to permit growth of the tumor. The UV6139SJ challenged mice were not irradiated.

b) Results

Administration of gp96 isolated from the UV6138 carcinoma rendered the mice immune to the UV6138 challenge but not the UV6139SJ challenge (FIG. 1). Conversely, administration of gp96 isolated from the UV6139SJ conferred resistance to the UV6139SJ cells but not to the UV6138 cells. The resistance rendered by the gp96 derived from the UV6138 against the UV6138 cells was much greater (6 out of 7 mice) than the resistance rendered by the gp96 derived from the UV6139SJ against the UV6139SJ cells (2 out of 4 mice) (FIG. 1). These results indicate that administration of gp96 preparations derived from the two UV-induced carcinomas immunized syngeneic mice from the respective cancer cell type and that the resistance rendered was greater and more uniform against the more immunogenic carcinoma cells.

6.2 Treatment Modality a) Materials and Methods

The ability of gp96 preparations to mediate therapy of pre-existing cancers was tested. Three groups of mice were injected intradermally with $10^7$ cells of the UV6139SJ carcinoma. The mice were kept under observation until the tumors became visible and palpable at day 4. Thereafter, the mice in the first group received no treatment, each mouse in the second group received every other day for a total of 5 injections of 6 micrograms each of gp96 derived from the UV6139SJ carcinoma cells, and each mouse in the third group received in a similar manner a total of 5 injections of gp96 derived from the normal liver.

b) Results

Tumor growth monitored as diameter width, was significantly retarded in mice treated with tumor-derived gp96 but not in mice treated with the liver-derived gp96 or in the untreated mice (FIG. 2). These results indicated a therapeutic effect of gp96-complexes in the UV6139SJ carcinoma model. All mice eventually succumbed to tumor growth. A scrutiny of the kinetics of tumor growth in treated and controlled mice shows that administration of tumor-derived gp96 had an immediate inhibitory effect on tumor growth and that the effect appears to have diminished after treatment with gp96 was terminated.

6.3 Measuring Generation of MHC Class I Restricted CDS$^+$ CTLs Provides an Assay for In Vivo Tumor Rejection The effect of vaccination with hsps has been measured thus far in the prior art by tumor rejection assays in vivo. While this assay is clearly the most demanding and rigorous evidence for immunogenicity, it is impractical for the purpose of monitoring immune response in humans. We tested the ability of tumor-derived gp96 preparations to elicit a CD8$^+$ T cell response in order to define an in vitro correlate for in vivo tumor rejection. Mice were immunized twice with 20 micrograms gp96 derived from 6138 or 6139SJ cells. Mixed lymphocyte-tumor cultures (MLTCs) generated from immunized mice were tested in a $^{51}$Chromium release assay and showed tumor-specific cytotoxicity for the tumor used as the source of gp96. This cytotoxic activity could be blocked by anti-MHC class I antibody K44 (Ozato, K., et al., 1985, *Proc. Natl. Acad. Sci. USA* 82:2427) (FIG. 3A) and by anti-CD8 antibody YTS169.4.(Cobbold, S. P., et al., 1984, *Nature* 312:548) (not shown). No corresponding activity was detected in MLTCs generated from spleens of naive mice. These results demonstrate that vaccination with gp96 elicits effective tumor-specific CTL response, which may be measured in vitro, and independently of the tumor regression responses shown in FIGS. 1 and 2. In light of the general paradigm that exogenous antigens are usually presented through MHC class II molecules and elicit a helper T cell response (Townsend, A. et al., 1989, *Ann. Rev. Immunol.* 7:601), the ability of exogenous HSP preparations to elicit MHC class I-restricted CTLs is unusual.

Figure 3A:
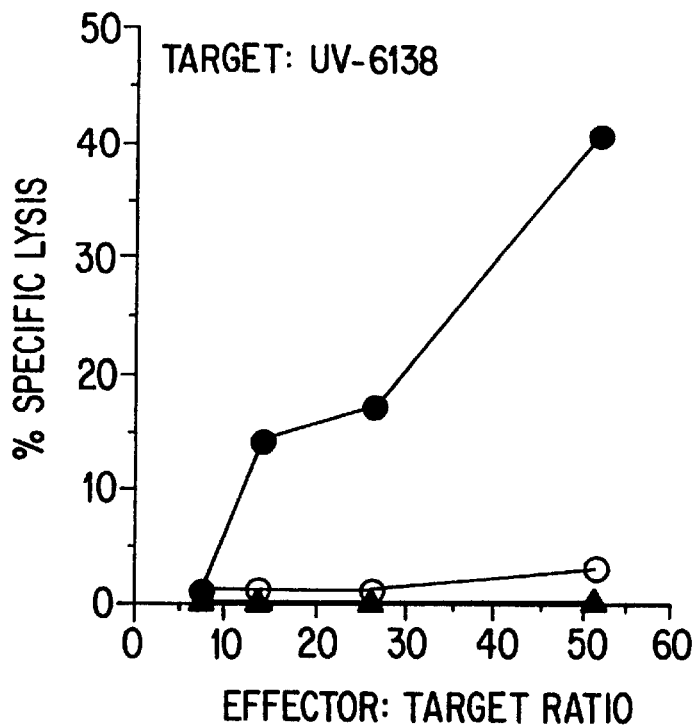
Figure 3B:
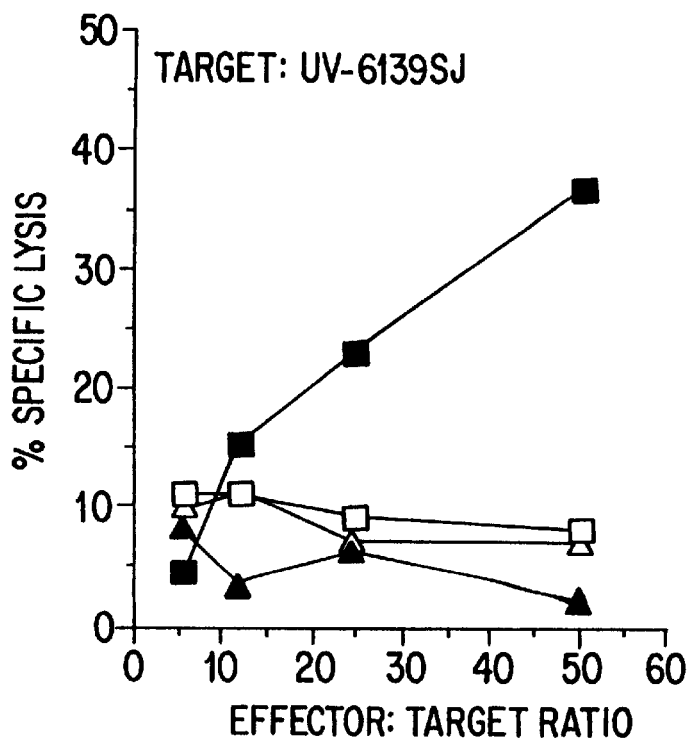
Figure 3C:
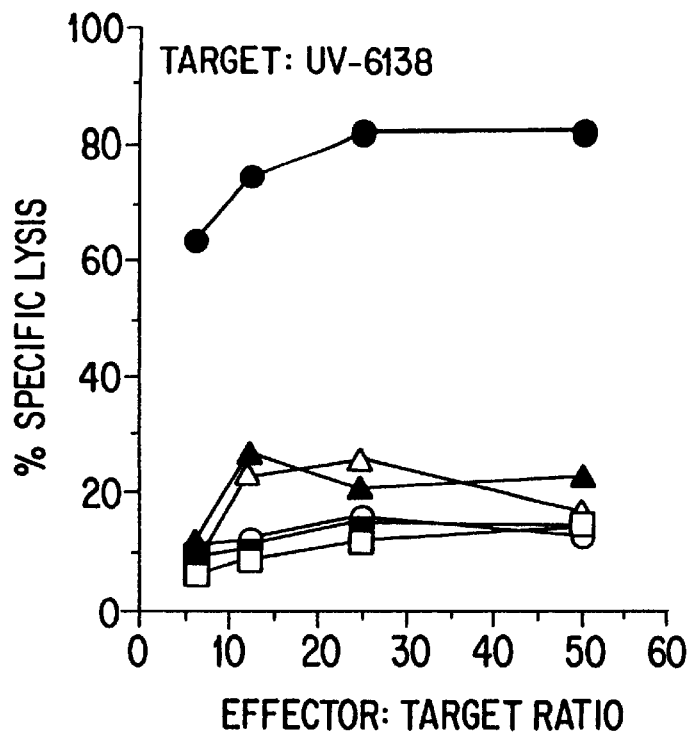
Figure 3D:
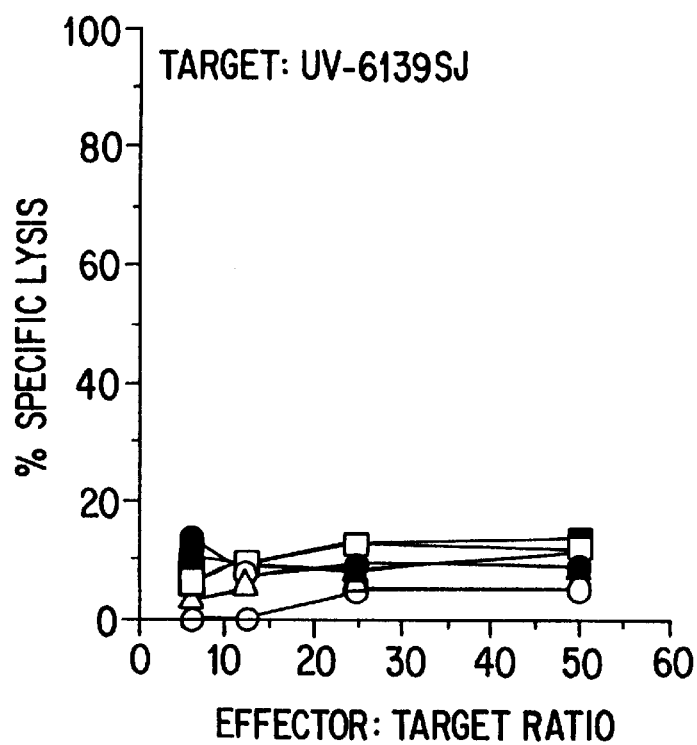
Figure 4A:
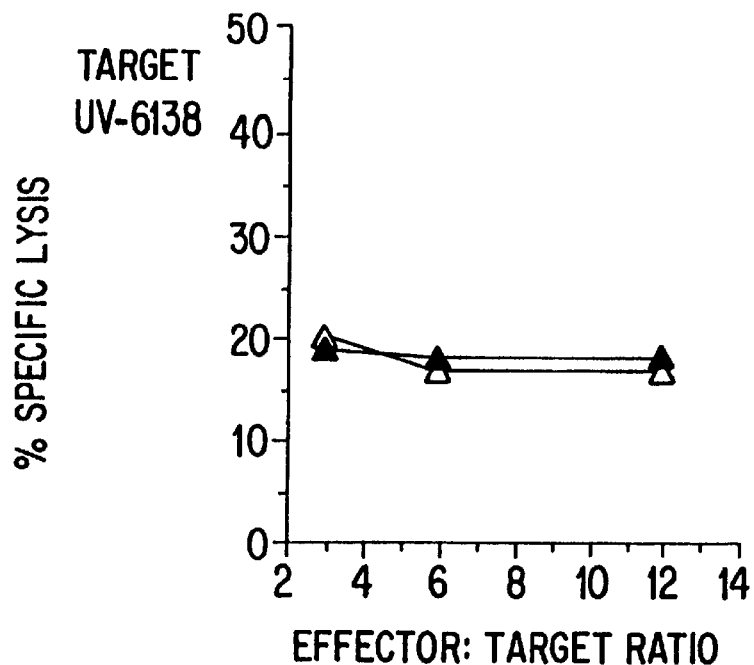
Figure 4B:
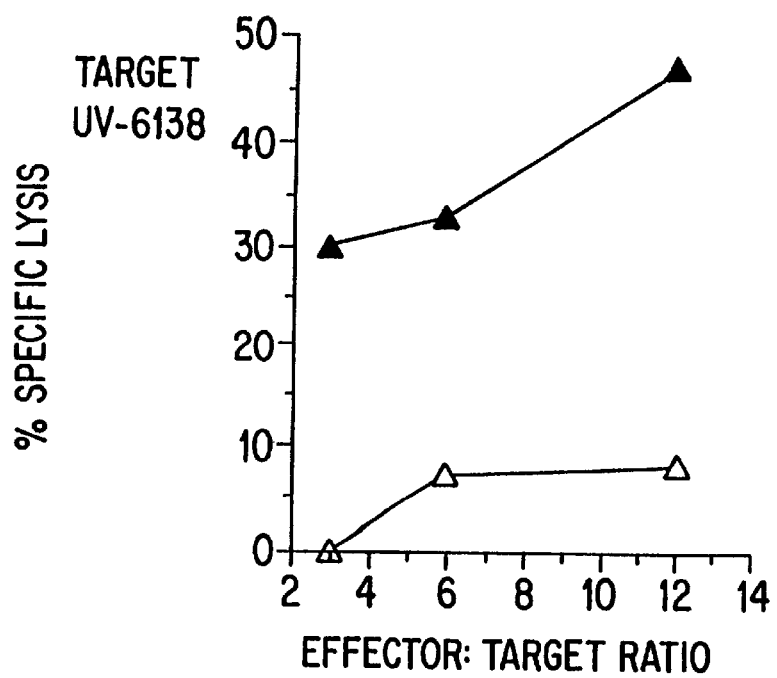
Figure 4C:
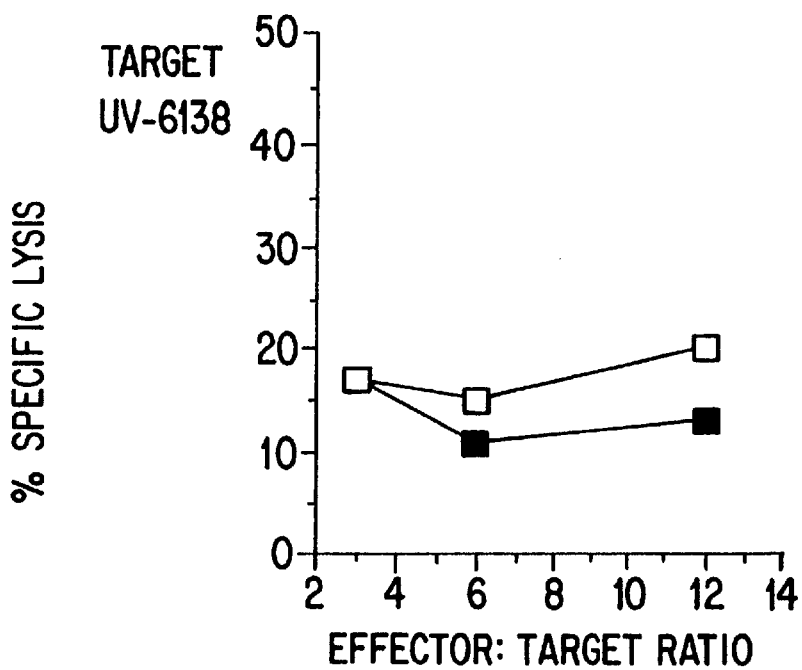
Figure 4D:
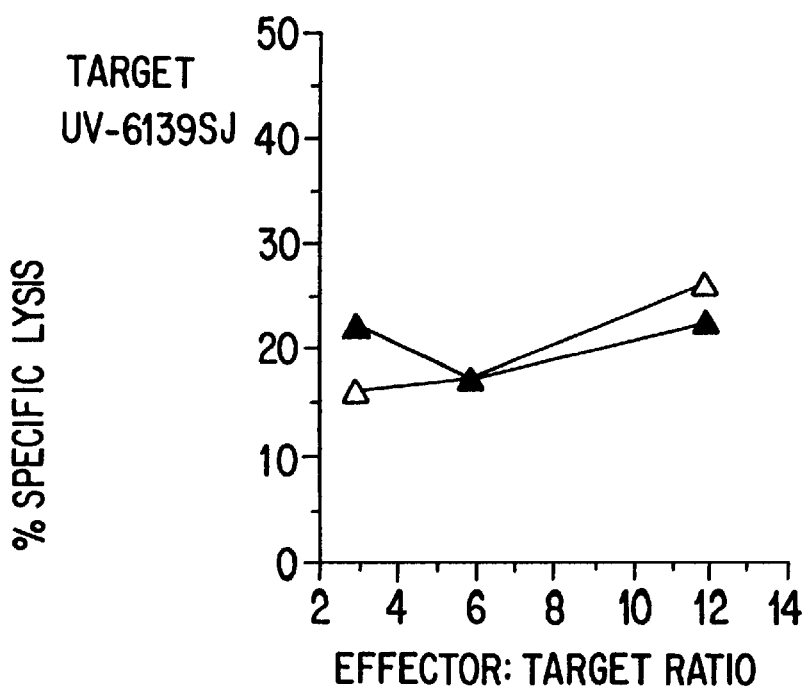
Figure 4E:
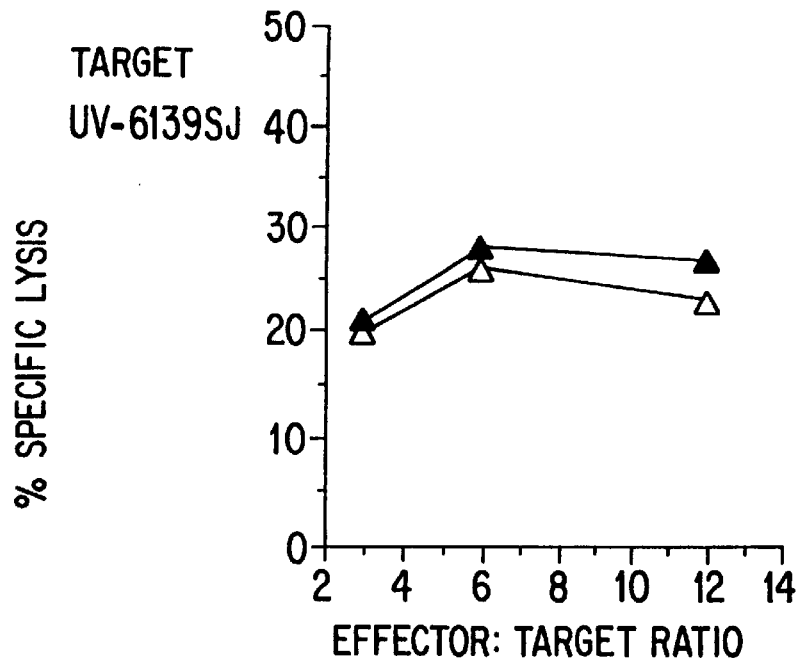
Figure 4F:
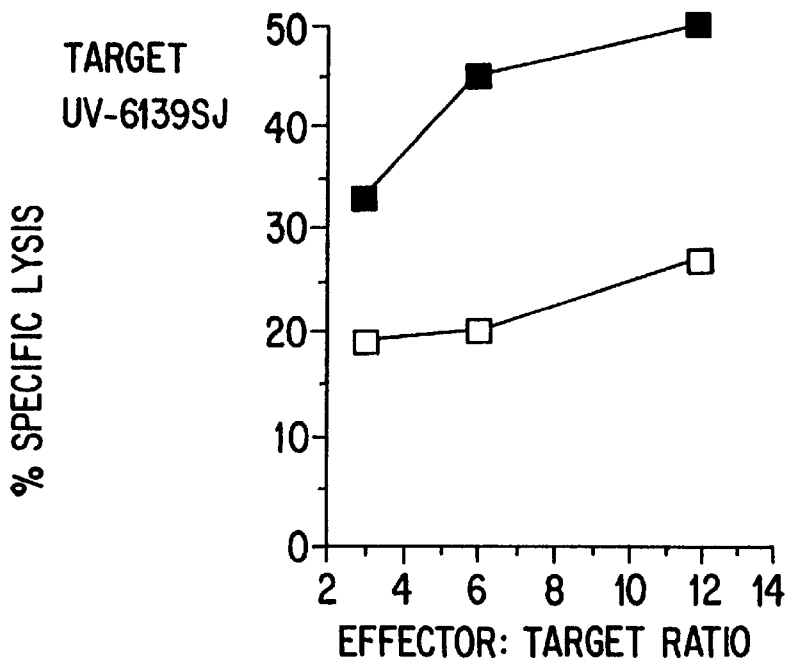

While testing the ability of tumor-derived gp96 preparations to elicit CTL responses, vaccination with irradiated whole tumor cells was carried out as a positive control. As expected, vaccination with intact irradiated 6138 cells led to vigorous tumor-specific CTL response. However, vaccination with intact irradiated 6139SJ cells did not lead to a corresponding CTL response (FIG. 3B). This result was surprising as UV-induced cancers of C3H mice are generally highly immunogenic (Kripke, M. L., 1977, *Cancer Res.* 37:1395. In view of the observation that 6139SJ cells are suitable targets for cytotoxic T cells (as seen in FIG. 3A), we deduce that they are not defective in antigen presentation; instead, their inability to elicit CTL response suggests that they are deficient in a crucial, as yet undefined step necessary specifically for priming a CTL response in vivo. It is most significant in this regard that although 6139SJ cells do not elicit a CTL response, gp96 preparations derived from them do so efficiently. This suggest that intact tumor cells and HSPs derived from them elicit immunity through distinct immunological pathways. The ability of gp96 preparations derived from a tumor to elicit a potent CTL response even when the tumor from which gp96 is derived is unable to do so, makes hsp preparations attractive as therapeutic vaccines.

6.4 GP96-Peptide Complexes Elicit a Memory T Cell Response

The ability to elicit a memory response is crucial for any vaccine and the ability of gp96 to elicit a memory T cell population was tested. A number of criteria, i.e., radiation resistance, kinetics of appearance, loss of CD45RB and L-selectin lymphocyte surface antigens, were used to identify memory T response. In contrast to naive T cells (Schrek, R., 1961, *Ann. N.Y. Acad. Sci* 95:839), memory T cells are cycling cells (Mackay, C. R., et al, 1992, *Nature* 360:264) and like other cycling lymphocytes, are resistant to sublethal irradiation (Lowenthal, J. W., et al., 1991, *Leuc. Biol.* 49:388). Thus radiation-resistance can be used to distinguish naive resting T cells from activated effector and memory T cells. However, no known surface markers distinguish activated effector T cells from memory T cells and the two are distinguishable only by the kinetics of their appearance. Activated effector T cells disappear from circulation within seven to ten days of depletion of significant quantities of antigen (Sprent, J., 1994, *Cell* 76:315); in contrast, memory T cells continue to circulate well beyond this window of time. In order to test, if vaccination with tumor-derived gp96 elicits a memory T cell response in addition to the effector response shown in FIG. 3, mice were vaccinated twice at ten day intervals, with tumor-derived gp96 and were irradiated (400 rad) twelve days. after the last vaccination. Three days after irradiation, MLTCs were generated from spleens of mice and tested for tumor-specific CTL response. It was observed (FIG. 4) that similar to the response in unirradiated mice (FIG. 3A), the irradiated, gp96-vaccinated mice generated powerful, MHC class I—restricted and tumor-specific CTL responses. Under this regimen of vaccination and irradiation, the irradiation eliminates the non-memory resting T cells, while the delay between the last vaccination and generation of MLTCs eliminates activated T lymphocytes (Sprent, J., 1994, *Cell* 76:315). Thus, the observed CTL response derives from radiation-resistant memory T cells elicited by gp96 preparations. This phenomenon was also tested in tumor rejection assays in vivo and mice vaccinated with pg96 and irradiated were observed to resist tumor challenges up to 17 days after vaccination, even though they had been irradiated (data not shown). These observations indicate that vaccination with gp96 elicits a long-lived, radiation-resistant T cell population.

As an independent parameter for memory response, expression of CD45RB (Birkeland, M. L., et al., 1989, *Proc. Natl. Acad. Sci. USA* 86:6734) on CD8$^+$ lymphocytes from irradiated and non-irradiated, naive and gp96-vaccinated mice was tested (FIG. 4). In each case, lymphocytes were obtained under the same regimen as described in the preceding paragraph, i.e., fifteen days after the last vaccination including three days after irradiation, in order to allow the activated effector cells to be depleted. It was observed that vaccination with gp96 led to relative loss of expression of CD45RB on CD8$^+$ T lymphocytes in irradiated as well as non-irradiated, immunized mice. Similar results were observed with L-selectin (data not shown). These results indicated that as judged from two independent sets of criteria, vaccination with gp96 elicits a memory T cell response. To the best of my knowledge, this is the first demonstration of generation of a memory CTL response by vaccination with a biochemically defined, purified cancer vaccine.

7. EXAMPLE

Administration of Hsp-Peptide Complexes in the Treatment of Hepatocellular Carcinoma Patients with hepatocellular carcinoma are injected with hsp-peptide complexes (derived from their own tumors or from other tumors) post surgery. Treatment with hsp-peptide complexes is started any time after surgery. However, if the patient has received chemotherapy, hsp-peptide complexes are usually administered after an, interval of four weeks or more so as to allow the immune system to recover. The immunocompetence of the patient is tested by procedures described in sections 5.7 above.

The therapeutic regimen of hsp-peptide complexes, for example, gp96, hsp90, hsp70 or a combination thereof, includes weekly injections of the hsp-peptide complex, dissolved in saline or other physiologically compatible solution.

The dosage used for hsp70 or gp96 is in the range of 10–600 micrograms, with the preferred dosage being 10–100 micrograms. The dosage used for hsp90 is in the range of 50 to 5,000 micrograms, with the preferred dosage being about 100 micrograms.

The route and site of injection is varied each time, for example, the first injection is given subcutaneously on the left arm, the second injection on the right arm, the third injection on the left abdominal region, the fourth injection on the right abdominal region, the fifth injection on the left thigh, the sixth injection on the right thigh, etc. The same site is repeated after a gap of one or more injections. In addition, injections are split and each half of the dose is administered at a different site on the same day.

Overall, the first four to six injections are given at weekly intervals. Subsequently, two injections are given at two-week intervals; followed by a regimen of injections at monthly intervals. The effect of hsp-peptide complexes therapy is monitored by measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology of tumors using techniques such as a computed tomographic (CT) scan; and e) changes in putative biomarkers of risk for a particular cancer in individuals at high risk.

Depending on the results obtained, as described above Section 5.7, the therapeutic regimen is developed to maintain and/or boost the immunological responses of the patient, with the ultimate goal of achieving tumor regression and complete eradication of cancer cells.

8. EXAMPLE

Administration of Hsp-Peptide Complexes in the Treatment of Colorectal Cancer Hsp-peptide complexes (gp96, hsp70, hsp90 or a combination thereof) are administered as adjuvant therapy and as prophylactic adjuvant therapy in patients after complete reduction of colorectal cancer to eliminate undetectable micrometastases and to improve survival.

The therapeutic and prophylactic regimens used in patients suffering from colorectal cancer are the same as those described in Section 7 above for patients recovering with hepatocellular carcinoma. The methods of monitoring of patients under clinical evaluation for prevention and treatment of colorectal cancer is done by procedures described in Section 5.7. Specifically, CEA levels are measured as a useful monitor of tumor regression and/or recurrence (Mayer, R. J., et al., 1978, *Cancer* 42:1428).

9. EXAMPLE

Method for Rapid Purification of Peptide-Associated Hsp70

Hsp70-peptide complexes can be readily obtained from cancer cells or cells infected by an infectious agent or other cells by a rapid, one-step ADP-agarose chromatography, described below.

9.1 Method and Results

Meth A sarcoma cells (500 million cells) were homogenized in hypotonic buffer and the lysate was centrifuged at 100,000 g for 90 minutes at 4° C. The supernatant was divided into two and was applied to an ADP-agarose or an ATP-agarose column. The columns were washed in buffer and were eluted with 3 mM ADP or 3 mM ATP, respectively. The eluted fractions were analyzed by SDS-PAGE: in both cases, apparently homogeneous preparations of hsp70 were obtained. However, when each of the preparations was tested for presence of peptides, the ADP-bound/eluted hsp70 preparation was found to be associated with peptides, while the ATP-bound/eluted hsp70 preparation was not. (FIGS. 5B and 5A, respectively).

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of treating or preventing an infectious disease in a human individual in whom such treatment or prevention is desired comprising administering to the individual a composition comprising an amount of a purified complex or purified population of complexes in the range of 50 to 5000 micrograms, said complex or complexes consisting essentially of a heat shock protein 90 noncovalently bound to an antigenic molecule, wherein the antigenic molecule of said complex or of at least one complex in said population displays the antigenicity of an antigen of an infectious agent that causes the infectious disease.

2. The method according to claim 1 in which the amount of the complex is 100 micrograms.

3. The method according to claim 1 in which the antigenic molecule is a peptide with which the heat shock protein is endogenously associated in cells infected with an infectious agent that causes the infectious disease.

4. The method according to claim 1 in which the antigenic molecule is an antigen of an infectious agent that causes the infectious disease.

5. The method according to claim 4 in which the infectious agent is a virus, bacterium, protozoan fungus, or parasite.

6. A kit comprising a container having a composition comprising an amount of a purified complex or purified population of complexes in the range of 50 to 5000 micrograms, said complex or complexes consisting essentially of heat shock protein 90 noncovalently bound to an antigenic molecule, wherein the antigenic molecule of said complex or of at least one complex in said population displays the antigenicity of an antigen of an infectious agent that causes an infectious disease.

7. The kit of claim 6 in which the amount of the complex is 100 micrograms.

8. The kit according to claim 6, in which the antigenic molecule is an antigen of an infectious agent that causes an infectious disease.

9. The kit according to claim 8, in which the infectious agent is a virus, bacterium, protozoan, fungus or parasite.

* * * * *